(12) United States Patent
Wu et al.

(10) Patent No.: US 10,196,662 B2
(45) Date of Patent: *Feb. 5, 2019

(54) COMPOSITION FOR PRODUCING MICRORNA PRECURSORS AS DRUGS FOR ENHANCING WOUND HEALING AND PRODUCTION METHOD OF THE MICRORNA PRECURSORS

(71) Applicant: MELLO BIOTECHNOLOGY INC., Santa Fe Springs, CA (US)

(72) Inventors: David T S Wu, Taipei (TW); Shi-Lung Lin, Arcadia, CA (US); Jack S. K. Chen, Diamond Bar, CA (US)

(73) Assignee: MELLO BIOTECHNOLOGY, INC., Santa Fe Springs, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/601,087

(22) Filed: Jan. 20, 2015

(65) Prior Publication Data

US 2015/0132805 A1  May 14, 2015

Related U.S. Application Data

(63) Continuation-in-part of application No. 13/572,263, filed on Aug. 10, 2012, now abandoned, and a continuation-in-part of application No. 13/964,705, filed on Aug. 12, 2013, now Pat. No. 9,422,559, and a continuation-in-part of application No. 14/502,608, filed on Sep. 30, 2014, now Pat. No. 9,783,811, and a continuation-in-part of application No. 14/527,439, filed on Oct. 29, 2014, now Pat. No. 9,637,747.

(51) Int. Cl.

| A61K 31/70 | (2006.01) |
|---|---|
| C12N 15/63 | (2006.01) |
| C12N 15/74 | (2006.01) |
| C12P 19/34 | (2006.01) |
| C12N 15/70 | (2006.01) |
| C12N 1/38 | (2006.01) |
| A01K 67/00 | (2006.01) |

(52) U.S. Cl.
CPC ............... *C12P 19/34* (2013.01); *C12N 1/38* (2013.01); *C12N 15/635* (2013.01); *C12N 15/70* (2013.01)

(58) Field of Classification Search
CPC ........... C12P 19/34; C12N 15/70; C12N 1/38; C12N 15/635
See application file for complete search history.

(56) References Cited

U.S. PATENT DOCUMENTS

| 4,879,226 A | 11/1989 | Wallace et al. |
|---|---|---|
| 5,464,758 A | 11/1995 | Gossen et al. |
| 7,064,186 B2 * | 6/2006 | Sprecher ............... A61K 38/00 435/69.5 |
| 7,943,318 B2 * | 5/2011 | Croce ................. C12Q 1/6886 435/6.14 |
| 7,959,926 B2 | 6/2011 | Buechler et al. |
| 7,968,311 B2 | 6/2011 | Mehta et al. |
| 9,879,263 B2 * | 1/2018 | Lin et al. |
| 2007/0099277 A1 | 5/2007 | Anderson et al. |
| 2008/0057034 A1 * | 3/2008 | Hassan ............. A61K 39/0258 424/93.2 |
| 2008/0293143 A1 * | 11/2008 | Lin ........................ C12N 15/63 435/456 |
| 2009/0203141 A1 | 8/2009 | Lin et al. |
| 2010/0088775 A1 * | 4/2010 | Khew-Goodall ........................... A61K 31/7088 800/13 |
| 2010/0240128 A1 | 9/2010 | Lin et al. |
| 2010/0272758 A1 * | 10/2010 | Woodard ........... A61K 39/0258 424/249.1 |
| 2011/0159552 A1 * | 6/2011 | Masuda ............... A61K 31/713 435/91.32 |
| 2011/0165680 A1 * | 7/2011 | Blattner ................ C12N 15/79 435/454 |

FOREIGN PATENT DOCUMENTS

| WO | WO 02/24904 | * | 3/2002 |
|---|---|---|---|
| WO | WO 2005/066797 A1 | | 6/2005 |
| WO | WO 2011/025566 A1 | | 3/2011 |

OTHER PUBLICATIONS

Neidhardt et al. Culture Medium for Enerobacteria. J. Bacteriology 119:736-747, 1974.*
Lewin et al. Viral promoters can initiate expression of toxin genes introduced into *Escherichia coli*. BMC Biotechnology 5: 19 doi:10.1186/1472-6750-5-19, 1-9 pages, 2005.*
Zhou et al. An RNA polymerase II construct syntehsizes short-hairpin RNA with a quantitative indicator and mediats highly efficient RNAi. Nucleic Acids Res. 33: e62; doi:10.1093/nar/gni061, 1-8 pages, 2005.*
Colón-González et al., "Anaerobic Growth does not Support Biofilm Formation in *Escherichia coli* K-12". Research in Microbiology, vol. 155 (2004) pp. 514-521.
Pantanella et al., "Violacein and Biofilm Production in Janthinobacterium Lividum", Journal of Applied Microbiology, vol. 102 (2007) pp. 992-999.

(Continued)

*Primary Examiner* — Quang Nguyen
(74) *Attorney, Agent, or Firm* — Birch, Stewart, Kolasch & Birch, LLP

(57) ABSTRACT

This invention generally relates to a composition and its production method useful for developing drugs and/or therapies for enhancing wound healing, in particular scarless wound healing. Particularly, the present invention teaches the essential processes necessary for producing and purifying embryonic stem cell (ESC)-specific RNA compositions, such as messenger RNAs (mRNA), microRNA precursors (pre-miRNA), and small hairpin RNAs (shRNA), which are useful for treating human diseases and lesions.

8 Claims, 17 Drawing Sheets
(13 of 17 Drawing Sheet(s) Filed in Color)
Specification includes a Sequence Listing.

(56) References Cited

OTHER PUBLICATIONS

Gossen et al., "Tight control of gene expression in mammalian cells by tetracycline-responsive prometers", Proceedings of the National Academy of Science, USA., vol. 89, Jun. 1992, pp. 5547-5551.

Kota et al., "Therapeutic microRNA Delivery Suppresses Tumorigenesis in a Murine Liver Cancer Model," Cell, vol. 137, Jun. 12, 2009, pp. 1005-1017.

Lin et al., "Gene silencing in vitro and in vivo using intronic microRNAs", Methods in Molecular Biology, vol. 342:MicroRNA Protocols, Edited by S. Ying, 2006, Humana Press, Totowa, New Jersey, pp. 295-312.

Lin et al., "Intron-mediated RNA interference and microRNA (miRNA)", Frontiers in Bioscience, vol. 13, Jan. 1, 2008, pp. 2216-2230.

Lin et al., "MicroRNA miR-302 inhibits the tumorigenecity of human pluripotent stem cells by coordinate suppression of CDK2 and CDK4/6 cell cycle pathways", Cancer Research, vol. 70, No. 22, Nov. 15, 2010, pp. 9473-9482.

Lin et al., "Mir-302 reprograms human skin cancer cells into a pluripoterl ES-cell-like state", RNA, vol. 14 (2008) pp. 2115-2124.

Lin et al., "Regulation of somatic cell reprogramming through inducible mir-302 expression", Nucleic Acids Research, vol. 39, No. 3 (2011) pp. 1054-1065.

Lin et al., "Role of mir-302 microRNA family in stem cell pluripotency and renewal", Edited by Ying Sy, Current Perspectives in MicroRNAs (miRNA), (2008) pp. 167-185.

Lin et al., "Transgene-like animal models using intronic microRNAs", Methods in Molecular Biology, vol. 342:MicroRNA Protocols, Edited by S. Ying. 2006, Humana Press, Totowa, New Jersey, pp. 321-334.

McDowell et al., "Determination of Intrinsic Transcription Termination Efficiency by RNA Polymerase Elongation Rate", Science, vol. 266 (1994) pp. 822-825.

Morille et al., Biomaterials 2008, 29:3477-3496.

Sibley et al., "Novel RNA-based Strategies for Therapeutic Gene Silencing," The American Society of Gene and Cell Therapy, vol. 18, No. 3, Mar. 2010 (Published Online: Jan. 19, 2010), pp. 466-476.

Simonsson et al., "DNA demethylation is necessary for the epigenetic reprogramming of somatic cell nuclei", Nature Cell Biology, vol. 6, No. 10, Oct. 2004, pp. 984-990.

\* cited by examiner

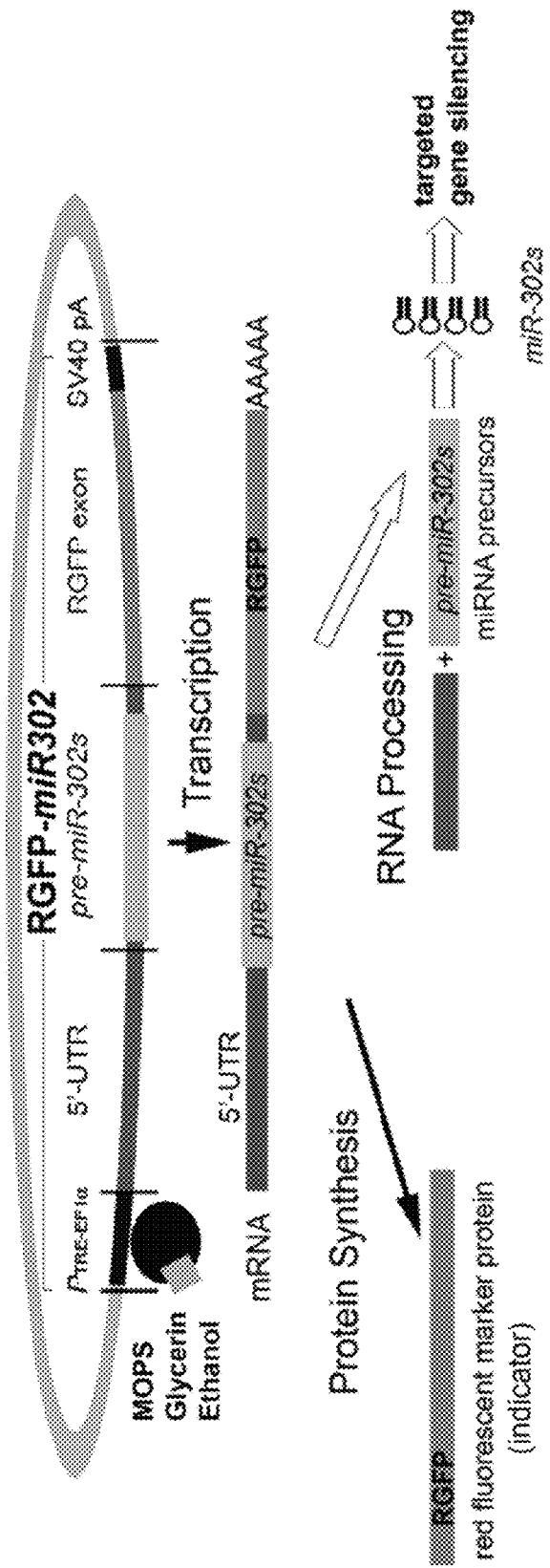

small RNAs extracted from blank *E. coli* competent cells (control):

FIG. 12

| | | | FIG.11A | FIG.11B | |
| | | | Group 1 | Group 2 | |
| | | | #1 | #2 | |
| Rpter Index | Reporter Name | p-value | Mean | Mean | Log2 (G2/G1) |
|---|---|---|---|---|---|
| 445 | hsa-miR-302c-5p | 1.28E-03 | 0 | 52,804 | 22.65 |
| 443 | hsa-miR-302a-5p | 1.38E-03 | 0 | 26,579 | 21.85 |
| 441 | hsa-miR-302a-3p | 1.52E-03 | 0 | 66,718 | 22.92 |
| 444 | hsa-miR-302c-3p | 3.51E-03 | 0 | 15,973 | 20.71 |
| 447 | hsa-miR-302d-5p | 2.27E-02 | 3 | 22,124 | 12.87 |
| 313 | hsa-miR-302b-5p | 3.09E-02 | 1 | 940 | 3.75 |
| 442 | hsa-miR-302d-3p | 4.86E-02 | 0 | 9,579 | 18.53 |
| 591 | hsa-miR-320b-3p | 4.88E-02 | 6 | 1,963 | 2.23 |
| 131 | hsa-miR-1275 | 8.78E-02 | 749 | 364 | -1.22 |
| Following transcripts are not statistically significant due to low signals (signal < 500) | | | | | |
| 554 | hsa-miR-3177-3p | 2.08E-02 | 402 | 76 | -2.40 |
| 986 | hsa-miR-4459 | 3.59E-02 | 66 | 135 | 1.04 |
| 967 | hsa-miR-4442 | 4.52E-02 | 32 | 65 | 1.02 |
| 1298 | hsa-miR-4758-5p | 4.85E-02 | 7 | 74 | 3.45 |
| 993 | hsa-miR-4466 | 5.70E-02 | 58 | 137 | 1.23 |
| 1120 | hsa-miR-4649-5p | 5.76E-02 | 187 | 385 | 1.04 |
| 1500 | hsa-miR-5195-3p | 5.81E-02 | 49 | 316 | 2.68 |
| 851 | hsa-miR-4253 | 5.86E-02 | 296 | 136 | -1.12 |
| 299 | hsa-miR-146a-5p | 5.93E-02 | 7 | 62 | 3.21 |
| 1156 | hsa-miR-4668-5p | 7.08E-02 | 315 | 70 | -2.17 |
| 974 | hsa-miR-4447 | 7.41E-02 | 13 | 89 | 2.76 |
| 1251 | hsa-miR-4728-3p | 7.96E-02 | 42 | 16 | -1.42 |
| 750 | hsa-miR-146a-3p | 8.97E-02 | 23 | 88 | 1.92 |
| 870 | hsa-miR-4270 | 9.39E-02 | 29 | 113 | 1.95 |
| 1123 | hsa-miR-4651 | 9.46E-02 | 25 | 116 | 2.19 |

FIG. 13A

Sequence of the miR-302 familial cluster (SEQ.ID.NO.13)

```
  1 AATTTTTTTC TTCTAAAGTT ATGCCATTTT GTTTTCTTTC TCCTCAGCTC TAAATACTCT      sequence of
 61 GAAGTCCAAA GAAGTTGTAT GTTGGGTGGG CTCCCCTTCAA CTTTAACATG GAAGTGCTTT      pro-miR-302b
121 CTGTGACTTT AAAAGTAAGT GCTTCCATGT TTTAGTAGGA GTGAATCCAA TTTACTTCTC
181 CAAAATAGAA CACGCTAACC TCATTTGAAG GGATCCCCTT TGCTTTAACA TGGGGTACC
                                                                          pro-miR-302c
241 TGCTGTGTGA AACAAAAGTA AGTGCTTCCA TGTTTCAGTG GAGGTGTCTC CAAGCCAGCA
301 CACCTTTTGT TACAAAATTT TTTTGTTATT GTGTTTTAAG GTTACTAAGC TTGTTACAGG
361 TTAAAGGATT CTAACTTTTT CCAAGACTGG GCTCCCCACC ACTTAAACGT GGATGTACTT
                                                                          pro-miR-302a
421 GCTTTGAAAC TAAAGAAGTA AGTGCTTCCA TGTTTTGGTG ATGGTAAGTC TTCTTTTTAC
481 ATTTTTATTA TTTTTTTAGA AAATAACTTT ATTGTATTGA CCGCAGCTCA TATATTTAAG
541 CTTTATTTTG TATTTTTACA TCTGTTAAGG GGCCCCCTCT ACTTTAACAT GGAGGCACTT      pro-miR-302d
601 GCTGTGACAT GACAAAAATA AGTGCTTCCA TGTTTGAGTG TGGTGGTTCC TACCTAATCA
661 GCAATTGAGT TAACGCCCAC ACTGTGTGCA GTTCTTGGCT ACAGGCCATT ACTGTTGCTA
```

FIG. 13B
pro-miR-302a (SEQ.ID.NO.6)
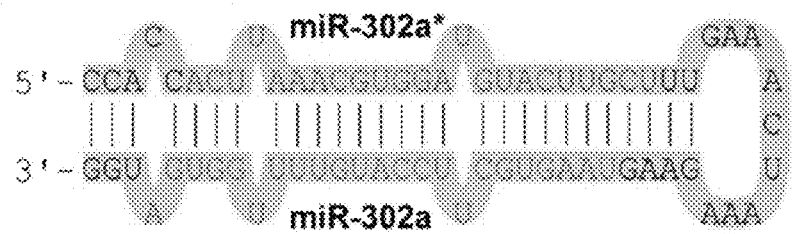
pro-miR-302b (SEQ.ID.NO.7)
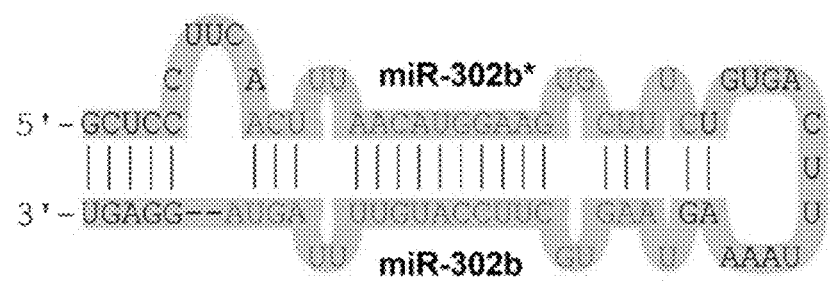
pro-miR-302c (SEQ.ID.NO.8)
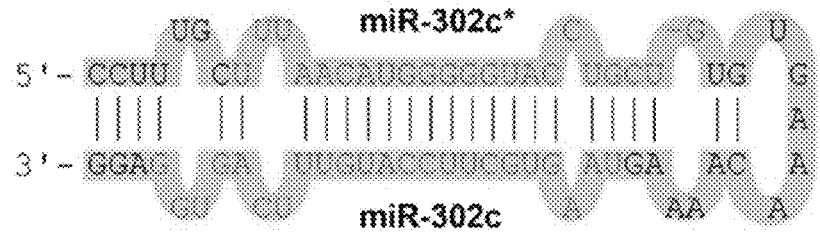
pro-miR-302d (SEQ.ID.NO.9)
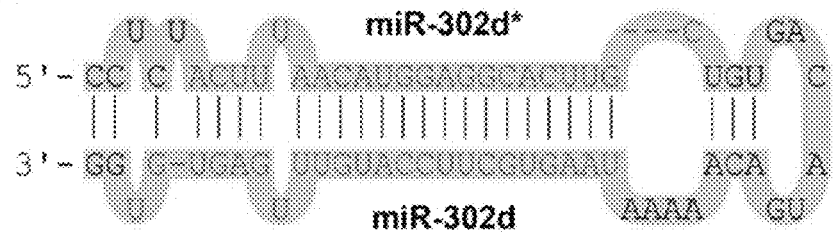

Example of control section shows large area of scar tissue underneath (no. 190-CR3)
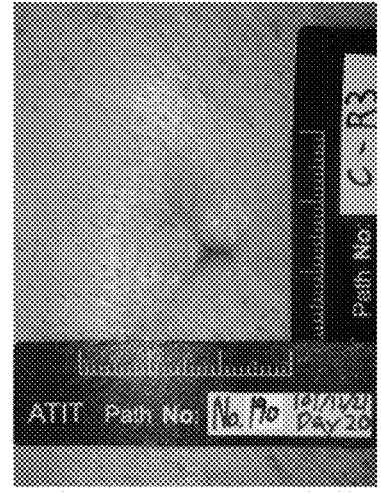
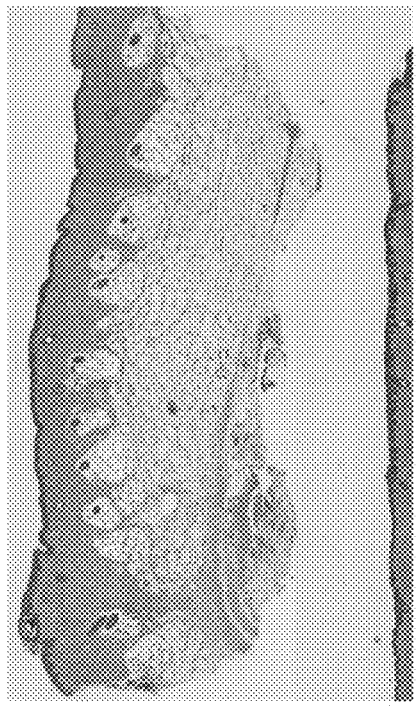
Example of treated section shows minimal scar tissue underneath (no. 190-BR2)
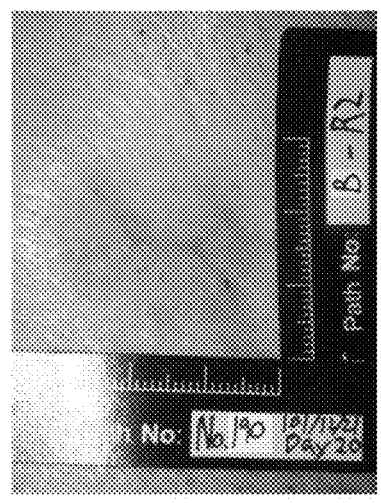
FIG. 17

SEQUENCE LISTING

<160> NUMBER OF SEQ ID NOS: 13

<210> SEQ ID NO 1
<211> LENGTH: 23
<212> TYPE: RNA
<213> ORGANISM: Artificial Sequence
<220> FEATURE:
<223> OTHER INFORMATION: Synthetic oligonucleotides

<400> SEQUENCE: 1
ucaccaaaac auggaagcac uua                                        23

<210> SEQ ID NO 2
<211> LENGTH: 23
<212> TYPE: RNA
<213> ORGANISM: Artificial Sequence
<220> FEATURE:
<223> OTHER INFORMATION: Synthetic oligonucleotides

<400> SEQUENCE: 2
acuuaaacgu ggauguacuu gcu                                        23

<210> SEQ ID NO 3

```
<211> LENGTH: 17
<212> TYPE: RNA
<213> ORGANISM: Artificial Sequence
<220> FEATURE:
<223> OTHER INFORMATION: Synthetic oligonucleotides

<400> SEQUENCE: 3
uaagugcuuc cauguuu                                                      17

<210> SEQ ID NO 4
<211> LENGTH: 69
<212> TYPE: RNA
<213> ORGANISM: Homo sapiens

<400> SEQUENCE: 4
ccaccacuua aacguggaug uacuugcuuu gaaacuaaag aaguaagugc uuccauguuu        60
uggugaugg                                                               69

<210> SEQ ID NO 5
<211> LENGTH: 720
<212> TYPE: RNA
<213> ORGANISM: Artificial Sequence
<220> FEATURE:
<223> OTHER INFORMATION: Synthetic oligonucleotides

<400> SEQUENCE: 5
aauuuuuuuc uucuaaaguu augccauuuu guuuucuuuc uccucagcuc uaaauacucu        60
gaaguccaaa gaaguuguau guugggugggg cucccuucaa cuuuaacaug gaagugcuuu     120 cuguqacuuu aaaaguaagu gcuuccaugu uuuaguagga gugaauccaa uuuacuucuc      180
caaaauagaa cacgcuaacc ucauuugaag ggauccccuu ugcuuuaaca uggggguacc      240
ugcuguguga aacaaaagua agugcuucca uguuucagug gaggugucuc caagccagca      300
caccuuuugu uacaaaauuu uuuuguuauu guguuuuaag guuacuaagc uuguuacagg      360
uuaaaggauu cuaacuuuuu ccaagacugg gcucccacc acuuaaacgu ggauguacuu       420
gcuuugaaac uaagaaguaa agugcuucca uguuuggug augguaaguc uucuuuuuac       480
auuuuuauua uuuuuuuaga aaauaacuuu auuguauuga ccgcagcuca uauauuuaag      540
cuuuauuuug uauuuuuaca ucuguuaagg ggccccucu acuuuaacau ggaggcacuu       600
gcugugacau gacaaaaaua agugcuucca uguugagug uggugguucc uaccuaauca       660
gcaauugagu uaacgcccac acugugugca guucuuggcu acaggccauu acuguugcua      720

<210> SEQ ID NO 6
<211> LENGTH: 69
<212> TYPE: RNA
<213> ORGANISM: Artificial Sequence
<220> FEATURE:
<223> OTHER INFORMATION: Synthetic oligonucleotides

<400> SEQUENCE: 6
ccaccacuua aacguggaug uacuugcuuu gaaacuaaag aaguaagugc uuccauguuu        60
uggugaugg                                                               69

<210> SEQ ID NO 7
<211> LENGTH: 73
<212> TYPE: RNA
<213> ORGANISM: Artificial Sequence
<220> FEATURE:
<223> OTHER INFORMATION: Synthetic oligonucleotides

<400> SEQUENCE: 7
```

```
gcucccuuca acuuuaacau ggaagugcuu ucugugacuu uaaaaguaag ugcuuccaug        60
uuuuaguagg agu                                                          73

<210> SEQ ID NO 8
<211> LENGTH: 68
<212> TYPE: RNA
<213> ORGANISM: Artificial Sequence
<220> FEATURE:
<223> OTHER INFORMATION: Synthetic oligonucleotides

<400> SEQUENCE: 8
ccuuugcuuu aacauggggg uaccugcugu gugaaacaaa aguaagugcu uccauguuuc        60
aguggagg                                                                68

<210> SEQ ID NO 9
<211> LENGTH: 68
<212> TYPE: RNA
<213> ORGANISM: Artificial Sequence
<220> FEATURE:
<223> OTHER INFORMATION: Synthetic oligonucleotides

<400> SEQUENCE: 9
ccucuacuuu aacauggagg cacuugcugu gacaugacaa aaauaagugc uuccauguuu       60
gagugugg                                                                68

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotides

<400> SEQUENCE: 10
tcactgaaac atggaagcac tta                                               23

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotides

<400> SEQUENCE: 11
gaggctggag cagaaggatt gctttgg                                           27

<210> SEQ ID NO 12
<211> LENGTH: 27
<212> TYPE: DNA
<213> ORGANISM: Artificial Sequence
<220> FEATURE:
<223> OTHER INFORMATION: Synthetic oligonucleotides

<400> SEQUENCE: 12
ccctcctgac ccatcacctc caccacc                                           27

<210> SEQ ID NO 13
<211> LENGTH: 720
<212> TYPE: DNA
<213> ORGANISM: Artificial Sequence
<220> FEATURE:
<223> OTHER INFORMATION: Synthetic oligonucleotides

<400> SEQUENCE: 13
```

```
aatttttttc ttctaaagtt atgccatttt gttttctttc tcctcagctc taaatactct    60
gaagtccaaa gaagttgtat gttgggtggg ctcccttcaa ctttaacatg gaagtgcttt   120
ctgtgacttt aaaagtaagt gcttccatgt tttagtagga gtgaatccaa tttacttctc   180
caaaatagaa cacgctaacc tcatttgaag ggatcccctt tgctttaaca tgggggtacc   240
tgctgtgtga aacaaaagta agtgcttcca tgtttcagtg gaggtgtctc caagccagca   300
caccttttgt tacaaaattt ttttgttatt gtgttttaag gttactaagc ttgttacagg   360
ttaaaggatt ctaactttt ccaagactgg gctccccacc acttaaacgt ggatgtactt    420
gctttgaaac taaagaagta agtgcttcca tgttttggtg atggtaagtc ttcttttac    480 attttatta ttttttaga aaataacttt attgtattga ccgcagctca tatatttaag    540
ctttattttg tatttttaca tctgttaagg ggcccctct actttaacat ggaggcactt    600
gctgtgacat gacaaaaata agtgcttcca tgtttgagtg tggtggttcc tacctaatca   660
gcaattgagt taacgcccac actgtgtgca gttcttggct acaggccatt actgttgcta   720
```

COMPOSITION FOR PRODUCING MICRORNA PRECURSORS AS DRUGS FOR ENHANCING WOUND HEALING AND PRODUCTION METHOD OF THE MICRORNA PRECURSORS

PRIORITY

The present invention claims priority to the U.S. patent application Ser. No. 13/572,263 filed on Aug. 10, 2012, entitled "An Inducible Gene Expression Composition for Using Eukaryotic Pol-2 Promoter-Driven Transcription in Prokaryotes and The Applications Thereof.", and the U.S. patent application Ser. No. 13/964,705 filed on Aug. 12, 2013, entitled "Production and Utilization of A Novel Anti-Cancer Drug in Therapy", and the U.S. patent application Ser. No. 14/502,608 filed on Sep. 30, 2014, entitled "An Inducible Gene Expression Composition for Using Eukaryotic Pol-2 Promoter-Driven Transcription in Prokaryotes and the Applications Thereof Application", and the U.S. patent application Ser. No. 14/527,439 filed on Oct. 29, 2014, entitled "Inducible Gene Expression Composition for Using Eukaryotic Pol-2 Promoter-Driven Transcription in Prokaryotes and The Applications Thereof". The entire contents of which are hereby all incorporated by reference as if fully set forth herein.

FIELD OF INVENTION

This invention generally relates to a composition and its production method useful for developing drugs and/or therapies for enhancing wound healing, in particular scarless wound healing. Particularly, the present invention teaches the essential processes necessary for producing and purifying embryonic stem cell (ESC)-specific RNA compositions, such as messenger RNAs (mRNA), microRNA precursors (pre-miRNA), and small hairpin RNAs (shRNA), which are useful for treating human diseases and lesions.

BACKGROUND

Stem cells are like a treasure box containing numerous effective ingredients useful for stimulating new cell growth/tissue regeneration, repairing and/or rejuvenating damaged/aged tissues, treating degenerative diseases, and preventing tumor/cancer formation/progression. Hence, it is conceivable that we can use these stem cells as a tool for novel drug screening, identification and production. As a result, the drugs so obtained will be useful for developing pharmaceutical and therapeutic applications, such as a biomedical utilization, device and/or apparatus for research, diagnosis, and/or therapy, and a combination thereof.

MicroRNA (miRNA) is one of the main effective ingredients in human embryonic stem cells (hESCs). Major hESC-specific miRNA species include, but not limited, members of the miR-302 family, miR-371~373 family, and miR-520 family. Among them, the miR-302 family has been found to play a functional role in tumor suppression (Lin et al., 2008 and 2010). MiR-302 contains eight (8) familial members, including four (4) sense miR-302 (a, b, c, and d) and four (4) antisense miR-302* (a*, b*, c*, and d*). These sense and antisense members are partially matched and can form double-stranded duplex, respectively. Precursors of miR-302 are formed by miR-302a and a* (pre-miR-302a), miR-302b and b* (pre-miR-302b), miR-302c and c* (miR-302c), and miR-302d and d* (pre-miR-302d) with a link sequence in one ends (stem loop) of the pre-miR-302a, the pre-miR-302b, the pre-miR-302c and the pre-miR-302d, respectively. In order to activate miR-302 function, miR-302 precursors (pre-miR-302s) are first processed into mature miR-302s by cellular RNase III Dicers and further form RNA-induced silencing complexes (RISCs) with certain argonaute proteins, subsequently leading to either RNA interference (RNAi)-directed degradation or translational suppression of targeted gene transcripts (mRNAs), in particular oncogene mRNAs (Lin et al., 2008, 2010 and 2011).

MiR-302 is the most abundant ncRNA (non-coding RNA) species found in hESCs and induced pluripotent stem cells (iPSCs). Our previous studies have shown that ectopic overexpression of miR-302 beyond the level found in hESCs is able to reprogram both human normal and cancerous cells to hESC-like iPSCs with a relatively slow cell cycle rate (20-24 hours/cycle) similar to that of a morula-stage early human zygote (Lin et al., 2008, 2010 and 2011; EP 2198025; U.S. Ser. No. 12/149,725; U.S. Ser. No. 12/318,806; U.S. Ser. No. 12/792,413). Relative quiescence is a defined characteristic of these miR-302-induced iPSCs, whereas hESCs and other previously reported four-factor-induced (either Oct4-Sox2-Klf4-c-Myc or Oct4-Sox2-Nanog-Lin28) iPSCs all showed a highly proliferative cell cycle rate (12-15 hours/cycle) similar to that of a tumor/cancer cell (Takahashi et al., 2006; Yu et al., 2007; Wernig et al., 2007; Wang et al., 2008). To disclose this tumor suppression effect of miR-302, we have identified the involvement of two miR-302-targeted G1-checkpoint regulators, including cyclin-dependent kinase 2 (CDK2) and cyclin D (Lin et al., 2010; U.S. Ser. No. 12/792,413; U.S. Ser. No. 13/964,705). It is known that cell cycle progression is driven by activities of cyclin-dependent kinases (CDKs), which forms functional complexes with positive regulatory subunits, cyclins, as well as by negative regulators, CDK inhibitors (CKIs, such as p14/p19Arf, p15Ink4b, p16Ink4a, p18Ink4c, p21Cip1/Waf1, and p27Kip1). In mammals, different cycling-CDK complexes are involved in regulating different cell cycle transitions, such as cyclin-D-CDK4/6 for G1-phase progression, cyclin-E-CDK2 for G1-S transition, cyclin-A-CDK2 for S-phase progression, and cyclin-A/B-CDC2 (cyclin-A/B-CDK1) for entry into M-phase. Hence, our studies suggested that the tumor suppression function of miR-302 results from co-suppression of the cyclin-E-CDK2 and cyclin-D-CDK4/6 pathways during G1-S transition.

Although miR-302 is useful for designing and developing novel anti-cancer drugs/vaccines, its production is problematic because natural miR-302 can only be found in human pluripotent stem cells such as hESCs, of which the resource is very limited. Alternatively, synthetic small interfering RNAs (siRNA) may be used to mimic pre-miR-302; yet, since the structure of a pre-miR-302 is formed by two mis-matched strands of miR-302 and miR-302*, those perfectly matched siRNA mimics can not replace the function of miR-302*, of which the sequence is totally different from the antisense strand of siRNA. For example, the antisense strand of siRNA-302a mimic is 5'-UCACCAAAAC AUG-GAAGCAC UUA-3' (SEQ.ID.NO.1), whereas native miR-302a* is 5'-ACUUAAACGU GGAUGUACUU GCU-3' (SEQ.ID.NO.2). As miR-302 function results from both of its sense miR-302 and antisense miR-302* strands, previous reports using those siRNA mimics have shown different results from native miR-302 function. On the other hand, our recent discovery of iPSCs may provide an alternative solution for pre-miR-302 production (EP 2198025; U.S. Ser. No. 12/149,725; U.S. Ser. No. 12/318,806). Nevertheless, the cost of growing these iPSCs is still too high to be used for industrial production.

Alternatively, the use of prokaryotic competent cells may be a possible approach for producing human microRNAs and their precursors. However, prokaryotic cells lack several essential enzymes required for eukaryotic microRNA expression and processing, such as Drosha and Dicer. Also, prokaryotic RNA polymerases do not efficiently transcribe small RNAs with high secondary structures, such as hairpin-like pre-miRNAs and shRNAs. In fact, there is no true microRNA encoded in bacterial genomes and bacteria do not naturally express microRNA. As a result, if we can force the expression of human microRNAs in prokaryotes, the resulting microRNAs will most likely remain in their precursor conformations similar to pri-miRNA (a large primary cluster of multiple pre-miRNAs) and/or pre-miRNA (one single hairpin RNA). Despite all of the above problems, the real challenge is how to force the expression of human microRNAs in prokaryotes. To overcome this major problem, our priority application U.S. Ser. No. 13/572,263 has established a preliminary method; yet, it is currently not sure whether these prokaryote-produced microRNAs (pro-miRNA) will possess the same structures and functions as their human counterparts. Also, the pro-miRNAs so obtained may be contaminated with bacterial endotoxin, which is not suitable for direct use in therapy.

As learning from current textbooks, every ordinary skill person in the art knows very well that prokaryotic and eukaryotic transcription machineries are different and hence not compatible to each other. For example, based on current understandings, eukaryotic RNA polymerases do not bind directly to a promoter sequence and require additional accessory proteins (cofactors) to initiate transcription, whereas prokaryotic RNA polymerases form a holoenzyme that binds directly to a promoter sequence to start transcription. It is also a common sense that eukaryotic messenger RNA (mRNA) is synthesized in the nucleus by type-II RNA polymerases (pol-2) and then processed and exported to the cytoplasm for protein synthesis, whereas prokaryotic RNA transcription and protein translation take place simultaneously off the same piece of DNA in the same place. This is because prokaryotes such as bacteria and archaea do not have any nucleus-like structure. Accordingly, these differences make a prokaryotic cell difficult or even impossible to produce eukaryotic RNAs using eukaryotic promoters.

In particular, it has been known that hairpin-like RNA structures are signals of intrinsic transcription termination in prokaryotic cells (McDowell et al., *Science* 1994) and hence make it impossible for prokaryotes to transcribe hairpin-like eukaryotic non-coding RNAs (ncRNA), such as microRNAs (miRNA) and small hairpin RNAs (shRNA).

Prior arts attempt at producing mammalian peptides and/or proteins in bacterial cells, such as US2007/0099277 to Anderson et al., U.S. Pat. No. 4,879,226 to Wallace et al., U.S. Pat. No. 7,959,926 to Buechler, and U.S. Pat. No. 7,968,311 to Mehta, used bacterial or bacteriophage promoters. For initiating expression, a desired gene was cloned into a plasmid vector driven by a bacterial or bacteriophage promoter. The gene must not contain any non-coding intron because bacteria do not have any RNA splicing machinery to process the intron. Then, the vector so obtained was introduced into a competent strain of bacterial cells, such as *Escherichia coli* (*E. coli*), for expressing the transcripts (mRNAs) of the gene and subsequently translating the mRNAs into proteins. Nevertheless, the bacterial and bacteriophage promoters, such as pProNde, pProNco, pET32, pUC19, pEKEX2, pEKEX2-2, pCFC, p15A, LacZ, Lac, lacUV5, Tac, Tc, T1, T3, T7, and SP6 RNA promoters, are not pol-2 promoters and their transcription activities tend to be an error-prone process which often causes mutations. In addition, Mehta further taught that glycerol/glycerin might be used to increase the efficiency of bacterial transformation; yet, no teaching was related to enhancement of RNA transcription, in particular pol-2 promoter-driven prokaryotic RNA transcription. Due to lack of possible compatibility between eukaryotic and prokaryotic transcription systems, these prior arts were still limited by the use of prokaryotic RNA promoters for gene expression in prokaryotes.

Due to the problems of system incompatibility and possible endotoxin contamination, there was previously no means for producing human pre-miRNA/shRNA-like drugs in prokaryotes. Also, a pre-miRNA/shRNA is sized about 70~85-nucleotides in length which is too large and costly to be made by a RNA synthesis machine. To overcome these problems, the present invention provides a novel breakthrough—By adding some defined chemicals mimicking certain transcriptional cofactors, we can create a novel adaptation environment for prokaryotic cells to use eukaryotic pol-2 and/or pol-2-like promoters for transcribing desired pre-miRNAs and shRNAs without going through error-prone prokaryotic promoters. The advantages are: first, cost-effective mass production due to the fast growth of bacteria; second, easy handling because of no need for growing dedicate hESCs or iPSCs; third, high fidelity productivity in terms of pol-2 promoter-driven RNA transcription; fourth, high purity of desired microRNAs due to lack of true microRNA in prokaryotes; and last, no endotoxin, which can be further removed by certain chemical treatments. Therefore, a method for producing human pre-miRNAs and/or shRNAs in prokaryotic cells without the problems of system incompatibility and endotoxin contamination is highly desirable. Furthermore, the drugs so obtained may present novel therapeutic effects other than the currently known function of synthetic microRNA mimics, such as siRNAs.

SUMMARY OF THE INVENTION

The principle of the present invention is relied on the different and incompatible properties between prokaryotic and eukaryotic RNA transcription systems. Naturally, prokaryotic RNA polymerases do not recognize eukaryotic promoters and vise versa. However, the present invention has identified chemical agents that can serve as transcriptional inducers to trigger and/or enhance eukaryotic promoter-driven RNA transcription in prokaryotes. Hence, the knowledge taught in the present invention is a totally novel breakthrough beyond all current understandings regarding the differences between prokaryotic and eukaryotic transcription systems.

The present invention is related to an inducible gene expression composition using certain chemical inducers to stimulate and/or enhance eukaryotic promoter-driven RNA transcription in prokaryotes. These chemical inducers have not been used in a cell culture medium due to their bacteriostatic and/or bactericidal properties, including 3-morpholinopropane-1-sulfonic acid [or named 3-(N-morpholino)propanesulfonic acid; MOPS], glycerin and ethanol, as well as their functional analogs such as 2-(N-morpholino) ethanesulfonic acid (MES), 4-(2-hydroxyethyl)-1-piperazineethanesulfonic acid (HEPES) and mannitol. Conceivably, chemicals with a similar structure like these transcriptional inducers may share a similar function. For example, MOPS is frequently used as a buffering agent in bacterial cell lysis and hence is not suitable for growing bacteria. On the other hand, ethanol is a well-known sanitizer and glycerin is frequently used in bacterial transformation by destabilizing the bacterial cell walls, indicating that glycerin is bacteriostatic and ethanol is bactericidal, respectively. In view of these known functionalities of MOPS, ethanol and glycerin, an ordinary skill in the art would not anticipate the use of a trace amount (0.001% to 4% volume/volume concentration) of these chemicals for inducing eukaryotic promoter-driven gene expression in prokaryotic cells without first knowing the knowledge of the present invention.

Based on the above knowledge, the present invention is a design and method for utilizing prokaryotic cells to produce human microRNA precursors (pre-miRNAs) and/or shRNAs as therapeutical drugs and/or vaccines for cancer therapy. More specifically, the present invention is a design and method of utilizing prokaryotic cells to produce a special kind of pre-miRNA-like agents, named pro-miRNA, that are capable of reprogramming the malignant properties of high-grade human cancer cells into a low-grade benign or even relatively normal-like state. Preferably, these pro-miRNAs are tumor suppressor microRNAs (TS-miRNA) similar to the precursors of miR-302a, b, c, d, e, and/or f (pre-miR-302s) and their natural familial cluster as well as their manually re-designed small hairpin RNA (shRNA) homologues/derivatives, and/or a combination thereof. The designs of pro-miRNA-like shRNA homologues/derivatives include imperfectly and perfectly matched hairpin conformations of the pro-miRNA and its homologous small interfering RNA (siRNA), which may be formed in a single unit or in a multiple unit cluster. Also, the mismatched part of a pro-miRNA-like shRNA can be located in either stem arm or loop region, containing about 30% to 100% homology to the desired pro-miRNA sequence(s). These designs may improve the target specificity and/or reduce the copy number of pro-miR-302 required for effective delivery and therapy. The human cells suitable for such a drug treatment include normal, tumor, and cancerous cells in vitro, ex vivo and/or in vivo.

Preferably, the prokaryotic cells used for the present invention are bacterial competent cells in particular, *Escherichia coli* (*E. coli*), and the chemical inducer is MOPS, ethanol, or glycerin, or a mixture thereof. Also preferably, the eukaryotic RNA promoter used is either a eukaryotic pol-2 promoter (i.e. EF1alpha promoter) or a pol-2 compatible (pol-2-like) viral promoter (i.e. cytomegaloviral CMV promoter). The gene mediated by the eukaryotic RNA promoter may code for either a non-coding or protein-coding RNA, or both (such as an intron-containing gene transcript), selected from the group consisting of microRNA (miRNA), small hairpin RNA (shRNA), small interfering RNA (siRNA), messenger RNA (mRNA), their precursors and homologues, and a combination thereof. For inducing gene expression, the prokaryotic cells are transfected with the eukaryotic RNA promoter-mediated gene and then grown in a culture medium similar to the bacterial culturing medium of Luria-Bertani (LB) broth at 37° C. with addition of the chemical inducer(s) for >24 hours.

To demonstrate the inducibility of said chemical inducers for human microRNA production in prokaryotes, we modified a lentiviral vector pSpRNAi-RGFP-miR302 from our priority U.S. patent application Ser. No. 12/149,725 and Ser. No. 12/318,806 to a new plasmid vector pLenti-EF1a-RGFP-miR302, of which the SpRNAi-RGFP gene expression is driven by a eukaryotic promoter such as EE1alpha or CMV (FIG. 1A). After that, we transformed *E. coli* competent cells with it and then used the production of red fluorescent protein (RGFP) as a visible marker for measuring the transcription rate and process of microRNA miR-302, as shown in FIG. 1B. Because the miR-302 familial cluster was also modified to be encoded in the 5'-intron region [e.g. 5'-untranslated region (5'-UTR) or the first intron] of the RGFP gene, the transcription of each RGFP mRNA led to the production of one 4-hairpin miR-302 precursor cluster (pri-miR-302) and/or four 1-hairpin miR-302 precursors (pre-miR-302s), as shown in FIGS. 5 and 6. Due to lack of RNase III Dicer in prokaryotes, the pri-miR-302 transcripts would be eventually broke down (by certain single-strand RNases in *E. coli*) into 1-hairpin pre-miR-302s, all of which could be extracted and further used as therapeutic drugs in the present invention. Broadly speaking, 5'-UTR and 3'-UTR are considered as a part of intron in the present invention.

All miR-302 members share a totally identical sequence in their first 5'-seventeen (17) nucleotides 5'-UAAGUGC-UUC CAUGUUU-3' (SEQ.ID.NO.3), and contain >82% homology in their full-length 23-nucleotides of a mature microRNA. Based on the results predicted by online computing programs TARGETSCAN (http://www.targetscan.org/) and PICTAR-VERT (http://pictar.mdc-berlin.de/), these miR-302s concurrently target against almost the same genes, including >600 human genes. In addition, miR-302 also shares many overlapping target genes with mir-92, mir-93, mir-200c, mir-367, mir-371, mir-372, mir-373, mir-374, and mir-520 familial members, all of which may possess similar functions. Most of these target genes are developmental signals and transcriptional factors involved in initiating and/or establishing certain lineage-specific cell differentiation during early embryogenesis (Lin et al., 2008). Many of these target genes are also well-known oncogenes; as a result, miR-302s likely functions as a tumor suppressor to prevent the deviation of normal hESC growth into tumor/cancer formation.

Induction of Eukaryotic Promoter-Driven Gene Expression in Prokaryotes.

*Escherichia coli* (*E. coli*) competent cells were transformed by the pLenti-EF1alpha-RGFP-miR302 plasmid (FIG. 1A) using a z-competent *E. coli* transformation kit (Zymo Research, Irvine, Calif.) and cultivated in Luria-Bertani (LB) broth supplemented with a mixture of 0.1% (v/v) MOPS and 0.05% (v/v) glycerin (inducers) at 37° C. with frequent agitation at 170 rpm. After overnight incubation, the transformed *E. coli* competent cells expressed highly abundant red RGFP proteins that could be clearly seen in the color of the LB broth, whereas the blank control *E. coli* presented no RGFP, as shown in FIG. 2. The presence of functional RGFP indicated that both of its encoded RNA and protein are successfully produced and processed in the competent cells.

To further confirm the specificity of gene expression induced by the chemical inducers, two transformed *E. coli* strains were prepared: one carried a pLVX-Grn-miR302+367 plasmid vector containing a CMV promoter-driven green fluorescent protein (GFP) gene and the other carried the aforementioned pLenti-EF1alpha-RGFP-miR302 vector. After overnight incubation with only 0.1% (v/v) MOPS, the *E. coli* transformed with pLVX-Grn-miR302+367 were changed to green color while the other with pLenti-EF1alpha-RGFP-miR302 still showed red color, as shown in FIG. 3. This result indicates that the chemical inducers like MOPS can stimulate a specific RNA transcription and it related protein production through either a eukaryotic pol-2 or a pol-2-like viral promoter. Particularly it was noted that the RGFP and GFP production is so abundant that even the *E. coli* cells are visually stained by the respective red and green colors. Conceivably, other chemicals containing a structure similar to MOPS, ethanol and/or glycerin may also have the same functionality in inducing and/or enhancing eukaryotic promoter-driven gene/RNA transcription in prokaryotic cells. These "transcription inducer" chemicals include, but not limited, mannitol, 2-(N-morpholino)ethanesulfonic acid (MES), and 4-(2-hydroxyethyl)-1-piperazineethanesulfonic acid (HEPES), or a mixture thereof.

Among all chemicals tested in the present invention, the top three most potent inducers are MOPS, glycerin and ethanol, as shown in FIG. 4. The quantitative result of the induced RGFP production was further confirmed by Western blot analysis, as shown in FIG. 5 and Example 3. Bacterial RuvB protein was served as a house-keeping standard to normalize RGFP expression. The inducibility of these identified inducers was also found to be dose-dependent in proportional to their concentrations. Without any treatment, negative control *E. coli* cells just showed their original color in absence of any fluorescent stain. Therefore, according to all these results, the present invention clearly provides a novel chemical-inducible composition and its application for modulating eukaryotic pol-2-driven or pol-2-like viral promoter-driven RNA production in prokaryotic cells. In view of the above demonstration, it is very obvious for an ordinary skill in the art to use other genes or the related cDNAs in place of the RGFP gene for producing functional RNAs and the related proteins in prokaryotes.

Induction of Eukaryotic Promoter-Driven microRNA Expression in Prokaryotes.

Accompanying the experiments of RGFP induction shown above, we further measured the expression of pri-/pre-miR-302s and their mature miR-302s in the pLenti-EF1alpha-RGFP-miR302-transformed cells with or without chemical induction. As shown in FIG. 6 and Example 4, the quantitative results of induced pri-/pre-miR-302 production have been confirmed by Northern blot analysis. Similar to the results of the RGFP induction in FIGS. 4 and 5, the pri-/pre-miR-302 expression was strongly detected in transformed cells treated with MOPS, glycerin or ethanol, but not blank control, indicating that these chemical inducers indeed stimulated the expression of the encoded pri-/pre-miRNAs in prokaryotic cells through a eukaryotic pol-2 promoter (FIG. 6). Due to the structural similarity of pre-miRNAs and shRNAs, it is obvious for an ordinary skill in the art to use the present invention to produce other kinds of pri-/pre-miRNA species, such as but not limited miR-34, miR-146, miR-371~373 and miR-520. For clarification, these prokaryote-produced pri-/pre-miRNAs are called pro-miRNAs.

Since pLenti-EF1alpha-RGFP-miR302 contains a miR-302 familial cluster located in the 5'-UTR of the RGFP gene (FIGS. 1A and 1B), the induced RGFP gene expression will also generate the miR-302 cluster (pri-miR-302) and its derivative pre-miR-302a, b, c and d (pre-miR-302s) as demonstrated in FIG. 1B. Due to lack of RNase III Dicer in prokaryotes, the pri-miR-302 and pre-miR-302s so obtained were found to remain as hairpin-like microRNA precursors, which are useful for developing therapeutic drugs. In human cells, these pre-miR-302s and pri-miR-302 can be processed into mature miR-302 for eliciting its tumor suppression function. Similarly, the present invention can also be used to produce other kinds of TS-miRNA (tumor suppressor microRNAs) species and their precursors, such as the miR-34a, miR-146a, miR-373 and miR-520 family.

The resulting pro-miRNAs can be easily extracted from competent *E. coli* cells (Examples 5 and 6) and further purified by high-performance liquid chromatography (HPLC) (FIGS. 10A and 10B). Within the purified pro-miR-302s, we have identified all of the miR-302 familial members (miR-302a, a*, b, b*, c, c*, d, and d*) using analyses of microRNA microarrays (FIGS. 11B and 12) and RNA sequencing [FIG. 13A (pri-miR-302) and 13B (pre-miR-302s)]. Particularly, the sequencing results showed that these pro-miR-302s all share exactly the same sequences as their natural pre-miR-302 counterparts (FIG. 13B). Furthermore, we have formulated these pro-miR-302s into a gel-like drug for testing their therapeutic effects on wound healing in vivo (Example 11), as shown in FIG. 14.

In the present invention, both of the vector and its encoded non-coding RNAs (i.e. pre-miRNA/shRNA and pri-miRNA) can be simultaneously amplified in the prokaryotic cells, preferably *E. coli* DH5alpha competent cells (Examples 1, 5 and 6). The method for isolating the amplified pLenti-EF1alpha-RGFP-miR302 plasmid DNA and the transcribed pri-/pre-miR-302s is described in Examples 5 and 6. The technology for delivering plasmid vectors (i.e. pLenti-EF1alpha-RGFP-miR302) into prokaryotic cells is called cell transformation, while the method for delivering the amplified non-coding RNAs (i.e. pro-/pri-/pre-miR-302s) into eukaryotic cells can be selected from the group consisting of endocytosis, chemical/glycerol infusion, peptide/liposomal/chemical-mediated transfection, electroporation, gene gun penetration, micro-injection, transposon/retrotransposon insertion and/or adenoviral/retroviral/lentiviral infection.

Pro-miR-302-Induced Pluripotent Stem Cell Derivation.

MiR-302 has been reported to reprogram mammalian somatic cells to human embryonic stem cell (hESC)-like induced pluripotent stem cells (iPSCs) as demonstrated in our priority U.S. patent application Ser. No. 12/149,725 and Ser. No. 12/318,806. Numerous stem cell applications and therapies have been designed and developed using these iPSCs. Nevertheless, since cultivating these iPSCs and hESCs is very costly and laborious, it is difficult and inefficient to collect miR-302 and its precursors from these pluripotent stem cells. On the other hand, making synthetic shRNA mimics is another possible alternative for pre-miR-302 production; yet, the cost is still very expensive. Also, the similarity between synthetic shRNA and natural pre-miR-302 is very questionable. To solve these problems, the present invention provides a simple, cheap and efficient method for mass production of pre-miR-302 in prokaryotes. Moreover, the extraction and purification of these prokaryote-produced pre-miR-302s (pro-miR-302s) is relatively easy and cost-effective, as shown in FIG. 6 and Example 6 of the present invention.

We have used the pLenti-EF1alpha-RGFP-miR302-transformed *E. coli* cells to produce and isolate high quantity and quality of pLenti-EF1alpha-RGFP-miR302 vector and pro-miR-302s, as shown in Examples 5 and 6. Both pLenti-EFIalpha-RGFP-miR302 and pro-miR-302s are useful for generating iPSCs. Following Example 2, when the pro-miR-302s produced by the present invention were transduced into human skin primary keratinocytes, the transfected keratinocytes were reprogrammed to hESC-like iPSCs that expressed strong hESC marker Oct4 (FIG. 7). In FIG. 8 and Example 8, we further performed bisulfite DNA sequencing assays to show that global DNA demethylation did occur in the promoters of both Oct4 and Sox2 genes, two of the key reprogramming factors as well as hESC markers. As global DNA demethylation and Oct4 expression are known to be the first step of somatic cell reprogramming to form hESC-like iPSCs (Simonsson and Gurdon, *Nat Cell Biol.* 6: 984-990, 2004), the pro-miR-302s isolated from the MOPS-induced *E. coli* cell extracts is proven to be as effective as natural pre-miR-302s, which are useful for iPSC derivation. Hence, pro-miR-302 and pre-miR-302 likely possess the same function in stem cell induction.

Utilization of Pro-miR-302 for Tumor/Cancer Therapy In Vivo.

Our previous studies have demonstrated the feasibility of this approach in treating human hepatocellular carcinoma HepG2 cells in vitro (Lin et al., 2010). As shown in FIG. 9, the treated tumor/cancer cells were reprogrammed to iPSCs (labeled as mirPS-HepG2) and formed embryoid body-like cell colonies. Moreover, miR-302 was also found to induce >95% apoptosis in the treated cancer cell population. The top panels of FIG. 9 further showed that flow cytometry analysis of the DNA content in response to cell cycle stages revealed a significant reduction in the mitotic cell populations after miR-302 treatments (form 45.6% to 17.2%). These results indicated that miR-302 can effectively attenuate the fast cell cycle rate of human cancers and hence causes significant apoptosis in these cancer cells.

Trials of Using Pro-microRNAs for Wound Healing Treatment in Mouse Skins.

We have tested the production of abundant microRNA miR-302 precursors (pre-miR-302s) and the related miR302-encoding plasmid vectors for use in a wound healing animal trial, using the present invention (Example 11). The pre-miR-302s and their related plasmid vectors were amplified as described in Examples 1 and 5 and extracted as described in Examples 5 and 6. Then, the isolated pre-miR-302s and their related plasmid vectors were mixed with a pre-prepared ointment base containing cocoa butter, cottonseed oil, olive oil, sodium pyruvate, and white petrolatum, namely F2 formula. The concentration of miR-302 precursors and vectors in the prepared ointment base is 10 µg/mL. Skin open wounds were generated by scalpel dissection. Ointment with or without miR-302 and/or pre-miR-302 was directly applied on the wound, respectively, and covered the whole wounded area. Then, the treated area was further sealed by liquid bandage. As show in FIG. 14, within two weeks, the results clearly showed that miR-302 and/or pre-miR-302 treatments significantly enhanced the speed of wound healing over twice faster than all other treatments and controls. Moreover, miR-302 and/or pre-miR-302-treated wound healing area showed normal hair regrowth and left no scar, while other treatments resulted in minor scar tissues with no hair (as indicated by black arrow).

Trials of Using Pro-microRNAs for Wound Healing Treatment in Pig (Porcine) Skins.

In this collaborative study with Animal Technology Institute Taiwan (ATIT), we aim to test the efficacy of miR-302-containing cell extracts (CCE) and purified miR-302 precursors (pre-miR-302) on healing of full-thickness wounds in pigs. These two testing materials were mixed with our special F2 formulation gel and topically applied to the wounds at selected time points for a total duration of 20 days. Visual observation clearly indicated that treatments with both miR-302 CCE and precursors resulted in significantly smaller wounds as compared to ones that received F2 gel alone. As shown in FIG. 15, the wounds in one of the animals (no. 190) seem to be almost completely healed by day 17 following treatments with miR-302 CCE and precursors, respectively, whereas the wound receiving F2 gels alone was still very noticeable. When the size of each wound was determined and used for calculating the percentage of wound closure at each time point, it can clearly be seen that treatments with both miR-302 CCE and precursors led to significantly higher healing rate as compared to the wounds treated with F2 gels alone (FIG. 16). Furthermore, histological staining revealed that purified miR-302 precursor-treated wounds exhibited fully tissue recovery and significantly scarless healing results compared to that of F2 gel-treated wounds, as shown in FIG. 17. In detail, as shown in FIG. 17, even though top view shows similar wound closure, cross sections consistently show different level of scar tissue formation. Taken together, the data presented here strongly indicated that both miR-302 CCE and precursors can promote fast and scarless healing in full-thickness wounds.

miR-302 CCE and its further purified miR-302 precursors (pre-mir-302) can also be used as novel skin care ingredients. Unlike other cosmetic and/or cosmeceutical products that use foreign extracts from non-human-derived materials that, miR-302 CCE contains highly concentrated human embryonic stem cell (hESC)-specific small non-coding nucleic acids, such as tRNA, snRNA, snoRNA and microRNA precursors. Pre-miR-302, on the other hand, is further purified from miR-302 CCE by removing other non-microRNA components. These hESC-specific microRNA precursors are hairpin-like small RNA molecules that can be easily delivered into skin cells with proper formulation due to their smaller size. These precursors can then be processed into mature and functional hESC-specific microRNAs, such as miR-302, that have been shown to play an important role in a wide range of cellular processes, such as wound healing and tissue repairing. Advantageously, we are now able to use a fast and cost-effective method to produce miR-302 CCE and precursors to present an additional option for wound care and address the problem of today's high cost of wound management.

A. Definitions

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more monomeric units of DNA and/or RNA, preferably more than three, and usually more than ten. An oligonucleotide longer than 13 nucleotide monomers is also called polynucleotide. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification, which may be selected from the group consisting of mRNA, hnRNA, rRNA, tRNA, snoRNA, snRNA, pre-microRNA, viral RNA and their RNA precursors as well as derivatives.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" or "*" symbol or with an "a" or "anti-sense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding.

Base Pair (bp): a partnership of adenine (A) with thymine (T), or of cytosine (C) with guanine (G) in a double stranded DNA molecule. In RNA, uracil (U) is substituted for thymine; hence, T and U are exchangeable to each other. Generally the partnership is achieved through hydrogen bonding. For example, a sense nucleotide sequence "5'-A-T-C-G-U-3'" can form complete base pairing with its antisense sequence "5'-A-C-G-A-T-3". Also, G and U may form non-Watson-and-Crick pairing, such as "5'-T-G-C-3'" pairing with "5'-G-U-A-3".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides. Also, thymine (T) and uracil (U) are homologous to each other.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3" is complementary to the sequence "5'-A-C-T-3", and also to "5'-A-C-U-3". Also, G and U may be complementary to each other in an RNA duplex or RNA-DNA pairing sequence. For example, the sequence "5'-U-G-C-3" is complementary to the sequence "5'-G-U-A-3", and also to "5'-G-U-G-3" as well as to "5'-G-C-G-3" and "5'-G-C-A-3". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration, such as DNA-DNA, DNA-RNA, and RNA-RNA duplexes as well as any duplex formed by pairing between partial DNA and partial RNA hybrid sequences.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with expression of intracellular genes containing either completely or partially complementarity to the small RNAs.

Gene Silencing Effect: a cell response after a gene function is suppressed, consisting but not limited of cell cycle attenuation, G0/G1-checkpoint arrest, tumor suppression, anti-tumorigenecity, cancer cell apoptosis, and a combination thereof.

Non-coding RNA: an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNA capable of binding to targeted gene transcripts (mRNAs) that have partial complementarity to the sequence of microRNA. Mature microRNA is usually sized about 17-27 oligonucleotides in length and is able to either directly degrade its intracellular mRNA target(s) or suppress the protein translation of its targeted mRNA(s), depending on the complementarity between the microRNA and its target mRNA(s). Native microRNAs are found in almost all eukaryotes, functioning as a defense against viral infections and allowing regulation of specific gene expression during development of plants and animals. In principle, one microRNA often targeted multiple target mRNAs to fulfill its full functionality while on the other hand multiple miRNAs may target the same gene transcripts to enhance the effect of gene silencing.

MicroRNA Precursor (Pre-miRNA): hairpin-like single-stranded RNA containing stem-arm and stem-loop regions for interacting with intracellular RNase III Dicer endoribonucleases to produce one or multiple mature microRNAs (miRNAs) capable of silencing a targeted gene or a specific group of targeted genes that contain full or partial complementarity to the mature microRNA sequence(s). The stem-arm of a pre-miRNA can form either a perfectly (100%) or a partially (mis-matched) hybrid duplexes, while the stem-loop connects one end of the stem-arm duplex to form a circle or hairpin-loop conformation required for being assembled into an RNA-induced silencing complex (RISC) with some argonaute proteins (AGO).

Prokaryote-produced MicroRNA Precursor (Pro-miRNA): hairpin-like RNA similar to natural microRNA precursor (pre-miRNA) but transcribed from an artificially recombinant microRNA-expressing plasmid driven by a eukaryotic promoter in prokaryotic competent cells. For example, pro-miR-302 is structurally as same as pre-miR-302 (FIGS. 13A and 13B) but transcribed from either a pLVX-Grn-miR302+367 or pLenti-EF1alpha-RGFP-miR302 vector in *E. coli* DH5alpha competent cells (Example 1). As prokaryotic cells normally do not express short RNAs with high secondary structures such as eukaryotic pre-miRNA, the production of pro-miRNA in prokaryotes usually requires the addition of chemical inducer(s) in order to stimulate the eukaryotic promoter-driven pre-miRNA transcription (FIGS. 2-4).

Small interfering RNA (siRNA): short double-stranded RNA sized about 18-27 perfectly base-paired ribonucleotide duplexes and capable of degrading target gene transcripts with almost perfect complementarity.

Small or short hairpin RNA (shRNA): single-stranded RNA that contains a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, or perhaps binds to, and initiates RNA transcription. For the purposes of the instant invention, a promoter can be a known polymerase or its cofactor binding site, an enhancer and the like, any sequence that can initiate synthesis of RNA transcripts by a desired polymerase.

Eukaryotic Promoter: a sequence of nucleic acid motifs which are required for RNA and/or gene transcription and can be recognized by eukaryotic type II RNA polymerases (pol-2), pol-2 equivalent, and/or pol-2 compatible (pol-2-like) viral polymerases for initiating the RNA/gene transcription.

Type-II RNA Polymerase (Pol-II or pol-2) Promoter: an RNA promoter that can be recognized by eukaryotic type-II RNA polymerases (Pol-II or pol-2) and hence is able to initiate the transcription of eukaryotic messenger RNAs (mRNAs) and/or microRNAs (miRNAs). For example, but not limited, a pol-2 promoter can be a mammalian RNA promoter or a cytomegaloviral (CMV) promoter.

Type-II RNA Polymerase (Pol-II or pol-2) Equivalent: a eukaryotic transcription machinery selected from the group consisting of mammalian type-II RNA polymerases (Pol-II or pol-2) and Pol-II compatible (pol-2-like) viral RNA polymerases.

Pol-II Compatible (pol-2-like) Viral Promoter: a viral RNA promoter capable of using the eukaryotic pol-2 or pol-2 equivalent transcription machineries for initiating gene and/or RNA expression. For example, but not limited, a pol-2-like viral promoter can be a cytomegaloviral (CMV) promoter or a retroviral long terminal repeat (LTR) promoter.

Cistron: a sequence of nucleotides in a DNA molecule coding for an amino acid residue sequence and including upstream and downstream DNA expression control elements.

Intron Excision: a cellular mechanism responsible for RNA processing, maturation and degradation, including RNA splicing, exosome digestion, nonsense-mediated decay (NMD) processing, and a combination thereof.

RNA Processing: a cellular mechanism responsible for RNA maturation, modification and degradation, including RNA splicing, intron excision, exosome digestion, nonsense-mediated decay (NMD), RNA editing, RNA processing, and a combination thereof.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Expression-Competent Vector: a linear or circular form of single- or double-stranded DNA selected form the group consisting of plasmid, viral vector, transposon, retrotransposon, DNA transgene, jumping gene, and a combination thereof.

Antibiotic Resistance Gene: a gene capable of degrading antibiotics selected from the group consisted of penicillin G, streptomycin, ampicillin (Amp), neomycin, G418, kanamycin, erythromycin, paromycin, phophomycin, spectromycin, tetracycline (Tet), doxycycline (Dox), rifapicin, amphotericin B, gentamycin, chloramphenicol, cephalothin, tylosin, and a combination thereof.

Restriction/Cloning Site: a DNA motif for restriction enzyme cleavage including but not limited AatII, AccI, AflII/III, AgeI, ApaI/LI, AseI, Asp718I, BamHI, BbeI, BclI/II, BglII, BsmI, Bsp120I, BspHI/LU11I/120I, BsrI/BI/GI, BssHII/SI, BstBI/U1/XI, ClaI, Csp6I, DpnI, DraI/II, EagI, Ecl136II, EcoRI/RII/47III/RV, EheI, FspI, HaeIII, HhaI, HinPI, HindIII, HinfI, HpaI/II, KasI, KpnI, MaeII/III, MfeI, MluI, MscI, MseI, NaeI, NarI, NcoI, NdeI, NgoMI, NotI, NruI, NsiI, PmlI, Ppu10I, PstI, PvuI/II, RsaI, SacI/II, SalI, Sau3AI, SmaI, SnaBI, SphI, SspI, StuI, TaiI, TaqI, XbaI, XhoI, XmaI cleavage site.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Cell Cycle Regulator: a cellular gene involved in controlling cell division and proliferation rates, consisting but not limited of CDK2, CDK4, CDK6, cyclins, BMI-1, p14/p19Arf, p15Ink4b, p16Ink4a, p18Ink4c, p21Cip1/Waf1, and p27Kip1, and a combination thereof.

Tumor Suppression Effect: a cellular anti-tumor and/or anti-cancer mechanism and response consisting of, but not limited, cell cycle attenuation, cell cycle arrest, inhibition of tumor cell growth, inhibition of cell tumorigenecity, inhibition of tumor/cancer cell transformation, induction of tumor/cancer cell apoptosis, induction of normal cell recovery, reprogramming high-grade malignant cancer cells to a more benign low-grade state (tumor regression), and a combination thereof.

Cancer Therapy Effect: a cell response and/or cellular mechanism resulted from a drug treatment, including, but not limited, inhibition of oncogene expression, inhibition of cancer cell proliferation, inhibition of cancer cell invasion and/or migration, inhibition of cancer metastasis, induction of cancer cell death, prevention of tumor/cancer formation, prevention of cancer relapse, suppression of cancer progression, repairing damaged tissue cells, reprogramming high-grade malignant cancers to a more benign low-grade state (cancer regression/remission), and a combination thereof.

Gene Silencing Effect: a cell response after a gene function is suppressed, consisting of but not limited, inhibition of oncogene expression, inhibition of cell proliferation, cell cycle arrest, tumor suppression, cancer regression, cancer prevention, cell apoptosis, cell repairing and/or rejuvenation, cell reprogramming, reprogramming diseased cells to a relatively normal state (spontaneous healing), and a combination thereof.

Cancer Reversion: a reprogramming mechanism that resets the malignant properties of high-grade cancers back to a relatively normal-like low-grade state in vitro, ex vivo or in vivo.

Targeted Cell: a single or a plurality of human cells selected from the group consisting of a somatic cell, a tissue, a stem cell, a germ-line cell, a teratoma cell, a tumor cell, a cancer cell, a damaged cell, an aged cell, and a combination thereof.

Prokaryote or Prokaryotic Cell: an one-cell organism that lacks a distinct membrane-bound nucleus and has its genetic materials in the form of a continuous strand of DNA, such as bacteria.

Eukaryote or Eukaryotic Cell: an one-cell or multiple-cell organism whose cells contain a nucleus and other structures (organelles) enclosed within membranes, such as yeast, plant and animal cells.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Transcription Inducer: a chemical agent that can induce and/or enhance eukaryotic RNA and/or gene transcription from a eukaryotic pol-2 or pol-2 equivalent promoter in prokaryotic cells. For example, a transcription inducer contains, but not limited, a chemical structure similar to 3-morpholinopropane-1-sulfonic acid (MOPS), ethanol and/or glycerin, as well as their functional analogs, such as mannitol, 2-(N-morpholino)ethanesulfonic acid (MES) and 4-(2-hydroxyethyl)-1-piperazineethanesulfonic acid (HEPES), or a mixture thereof.

Antibody: a peptide or protein molecule having a pre-selected conserved domain structure coding for a receptor capable of binding a pre-selected ligand.

Pharmaceutical and/or Therapeutic Application: a biomedical utilization, device and/or apparatus useful for diagnosis, stem cell generation, stem cell research and/or therapy development, tissue/organ repair and/or rejuvenation, wound healing treatment, tumor suppression, cancer therapy and/or prevention, disease treatment, drug production, and a combination thereof.

B. Compositions and Applications

A composition and method for producing a new kind of prokaryote-produced microRNA precursors (pro-miRNAs) capable of reprogramming the malignant properties of human cancers into a low-grade benign or normal-like state in vitro, ex vivo and in vivo, comprising: (a) at least a chemical inducer agent containing a structure similar to 3-morpholinopropane-1-sulfonic acid (MOPS), ethanol, or glycerin, or a mixture thereof; and (b) a plurality of prokaryotic cells that contain at least a pre-miRNA-encoding gene mediated by eukaryotic pol-2 and/or pol-2-like promoter-driven transcription; wherein said (a) and (b) are mixed together under a condition to induce the expression of said gene, so as to generate the encoded pre-miRNA in the prokaryotic cells. Notably, the chemical inducer is able to stimulate eukaryotic promoter-driven RNA transcription in prokaryotes!

In principle, the present invention provides a novel composition design and its applicable strategy for inducing a quick adaptation of prokaryotes to use eukaryotic pol-2 and pol-2-like promoters for directly expressing certain desired microRNA precursors (pre-miRNA) without the need of using error-prone prokaryotic promoters or growing laborious and costly hybridomas or mammalian cells.

Preferably, said prokaryote is a bacterial cell strain in particular, Escherichia coli (E. coli), and said chemical inducer is 3-morpholinopropane-1-sulfonic acid (MOPS), ethanol, or glycerin, or a mixture thereof. Also preferably, said eukaryotic promoter is either a eukaryotic pol-2 promoter, such as EF1 alpha, or a pol-2 compatible (pol-2-like) viral promoter, such as cytomegaloviral (CMV) promoter or retroviral long terminal repeat (LTR) promoter. The pre-miRNA-encoding gene mediated by said eukaryotic promoter is coded for either a non-coding or a protein-coding RNA transcript, or both (such as an intron-containing gene transcript), selected from the group consisting of microRNA (miRNA), small hairpin RNA (shRNA), small interfering RNA (siRNA), messenger RNA (mRNA) and their precursors as well as shRNA/siRNA homologues, and a combination thereof. The protein-coding RNA may be selected from, but not limited to, the group consisting of a gene encoding enzyme, growth factor, antibody, insulin, botulinum toxin (botox), a functional protein and/or its analogs, and a combination thereof. Preferably, said condition for inducing the expression of said pre-miRNA-encoding gene is a bacterial culturing condition such as Luria-Bertani (LB) broth at 37° C. with the addition of said chemical inducer(s).

BRIEF DESCRIPTION OF THE DRAWINGS

The patent or application file contains at least one color drawing. Copies of this patent or patent application publication with color drawing will be provided by the USPTO upon request and payment of the necessary fee.

Referring particularly to the drawings for the purpose of illustration only and not limitation, there is illustrated:

FIGS. 1A and 1B show a eukaryotic promoter-driven expression vector composition (1A) and its expression mechanism (1B) for RNA transcript and/or protein production in prokaryotes. For demonstrating the present invention, a new pLenti-EF1alpha-RGFP-miR302 vector (FIG. 1A) is served as an example composition for transforming E. coli DH5alpha competent cells to produce RGFP proteins as well as miR-302s and their precursors (pre-miR-302s) under the stimulation of MOPS, glycerin and/or ethanol. pLenti-EF1alpha-RGFP-miR302 is a lentiviral plasmid vector that is designed by the inventors to expresses various microRNAs/shRNAs, mRNAs and/or proteins/peptides in both prokaryotes and eukaryotes. According to the disclosed mechanism (1B), it is easy for an ordinary skill in the art to use any microRNA/shRNA in place miR-302 or any mRNA/protein in place of RGFP as described in the present invention. Black arrows indicate the pathways occurring in both prokaryotic and eukaryotic cells, while blank arrows indicate the steps only occurring in the eukaryotic cells.

FIG. 11A shows that RNAs from blank *E. coli* cells present almost no microRNA (green dots mean non-statistically significant whereas red dots indicate positive results). This is because prokaryotes lack several essential enzymes required for microRNA expression and processing, such as Pol-2, Drosha and RNase III Dicer. Also, prokaryotic RNA polymerases do not efficiently transcribe small RNAs with high secondary structures, such as hairpin-like pre-miRNAs and shRNAs. As a result, only using the present invention we can stimulate the expression of specific microRNAs, such as miR-302a, a*, b, b*, c, c*, d and d* as shown in FIG. 11B, in prokaryotic cells. Since prokaryotic cells possess no Dicer, all microRNAs remain in their precursor conformations, such as pri-miRNA (4-hairpin cluster) and/or pre-miRNA (1 hairpin precursor). Taken together, the results of FIGS. 10B and 11B have established two facts as: (1) small RNAs extracted from the RGFP-miR302-transfected cells contain mostly pure miR-302 precursors, and (2) there is almost no other kind of microRNA contamination in the *E. coli* competent cells.

FIG. 12 shows the lists of expressed microRNAs extracted from either blank *E. coli* competent cells (Group 1 as shown in FIG. 11A) or pLenti-EF1alpha-RGFP-miR302-transfected cells (Group 2 as shown in FIG. 11B). Signals less than 500 are not statistically significant (as shown in green in FIGS. 11A and 11B), which may be caused by either low copy number expression or high background.

FIGS. 13A and 13B show the sequencing results of the miR-302 familial cluster (family) (13A, SEQ.ID.NO.13, wherein the sequences of pro-miR-302a, pro-miR-302b, pro-miR-302c, and pro-miR-302d are underlined) and the individual pro-miR-302a (SEQ.ID.NO.6), pro-miR-302b (SEQ.ID.NO.7), pro-miR-302c (SEQ.ID.NO.8), and pro-miR-302d (SEQ.ID.NO.9) sequences (13B). After transcription, the sequence of the miR-302 familial cluster (=pri-miR-302) is 5'-AAUUUUUUC UUCUAAAGUU AUGCCAUUUU GUUUUCUUUC UCCUCAGCUC UAAAUACUCU GAAGUCCAAA GAAGUUGUAU GUUGGGUGGG CUCCCUUCAA CUUUAACAUG GAAGUGCUUU CUGUGACUUU AAAAGUAAGU GCUUCCAUGU UUUAGUAGGA GUGAAUCCAA UUUACUUCUC CAAAAUAGAA CACGCUAACC UCAUUUGAAG GGAUCCCUU UGCUUUAACA UGGGGGUACC UGCUGUGUGA AACAAAAGUA AGUGCUUCCA UGUUUCAGUG GAGGUGUCUC CAAGCCAGCA CACCUUUUGU UACAAAAUUU UUUUGUUAUU GUGUUUUAAG GUUACUAAGC UUGUUACAGG UUAAAGGAUU CUAACUUUUU CCAAGACUGG GCUCCCCACC ACUUAAACGU GGAUGACUU GCUUUGAAAC UAAAGAAGUA AGUGCUUCCA UGUUUUGGUG AUGGUAAGUC UUCUUUUUAC AUUUUUAUUA UUUUUUUAGA AAAUAACUUU AUUGUAUUGA CCGCAGCUCA UAUAUUUAAG CUUUAUUUUG UAUUUUUACA UCUGUUAAGG GGCCCCCUCU ACUUUAACAU GGAGGCACUU GCUGUGACAU GACAAAAAUA AGUGCUUCCA UGUUUGAGUG UGGUGGUUCC UACCUAAUCA GCAAUUGAGU UAACGCCCAC ACUGUGUGCA GUUCUUGGCU ACAGGCCAUU ACUGUUGCUA-3' (SEQ.ID.NO.5), while the individual sequences of pro-miR-302a, pro-miR-302b, pro-miR-302c, and pro-miR-302d are as follows: 5'-CCACCACUUA AACGUGGAUG UACUUGCUUU GAAACUAAAG AAGUAAGUGC UUCCAUGUUU UGGUGAUGG-3' (SEQ.ID.NO.6), 5'-GCUCCCUUCA ACUUUAACAU GGAAGUGCUU UCUGUGACUU UAAAAGUAAG UGCUUCCAUG UUUAGUAGG AGU-3' (SEQ.ID.NO.7), 5'-CCUUUGCUUU AACAUGGGGG UACCUGCUGU GUGAAACAAA AGUAAGUGCU UCCAUGUUUC AGUGGAGG-3' (SEQ.ID.NO.8), and 5'-CCUCUACUUU AACAUGGAGG CACUUGCUGU GACAUGACAA AAAUAAGUGC UUCCAUGUUU GAGUGUGG-3' (SEQ.ID.NO.9), respectively.

FIG. 17 shows histological staining (Hematoxylin and Eosin) reveals significantly less scar (scarless) tissue recovery in wounds treated with miR-302 precursors (5/6). Tissue samples were collected from each wound and used for preparing histological sections for H&E staining. For example, this figure shows the extent of scar tissue formation in wounds treated with miR-302 precursors (left) and F2 gel alone (right) in one of the treated animals (no. 190) on day 20. Total tested sample number n=6 for each treatment. The test shows 80 percent and up of scarless healing effect.

EXAMPLES

In the experimental disclosure which follows, the following abbreviations apply: M (molar); mM (millimolar); μm (micromolar); mol (moles); pmol (picomoles); gm (grams); mg (milligrams); μg (micrograms); ng (nanograms); L (liters); ml (milliliters); μl (microliters); ° C. (degrees Centigrade); RNA (ribonucleic acid); DNA (deoxyribonucleic acid); dNTP (deoxyribonucleotide triphosphate); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); ATCC (American Type Culture Collection, Rockville, Md.); hESC (human embryonic stem cells); and iPSC (induced pluripotent stem cells).

1. Bacterial Cell Culture and Chemical Treatments

Figure 1A:
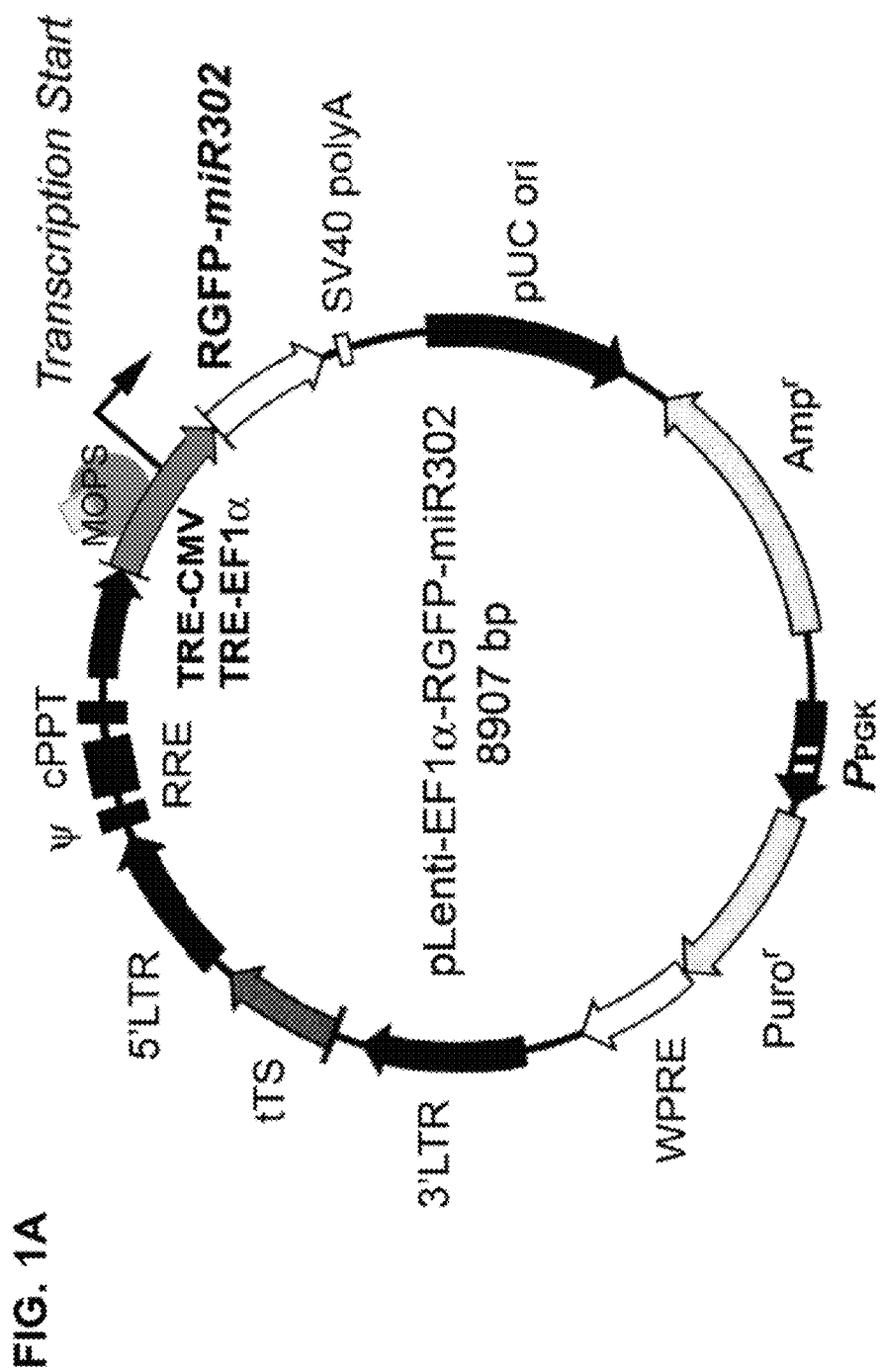
Figure 2:
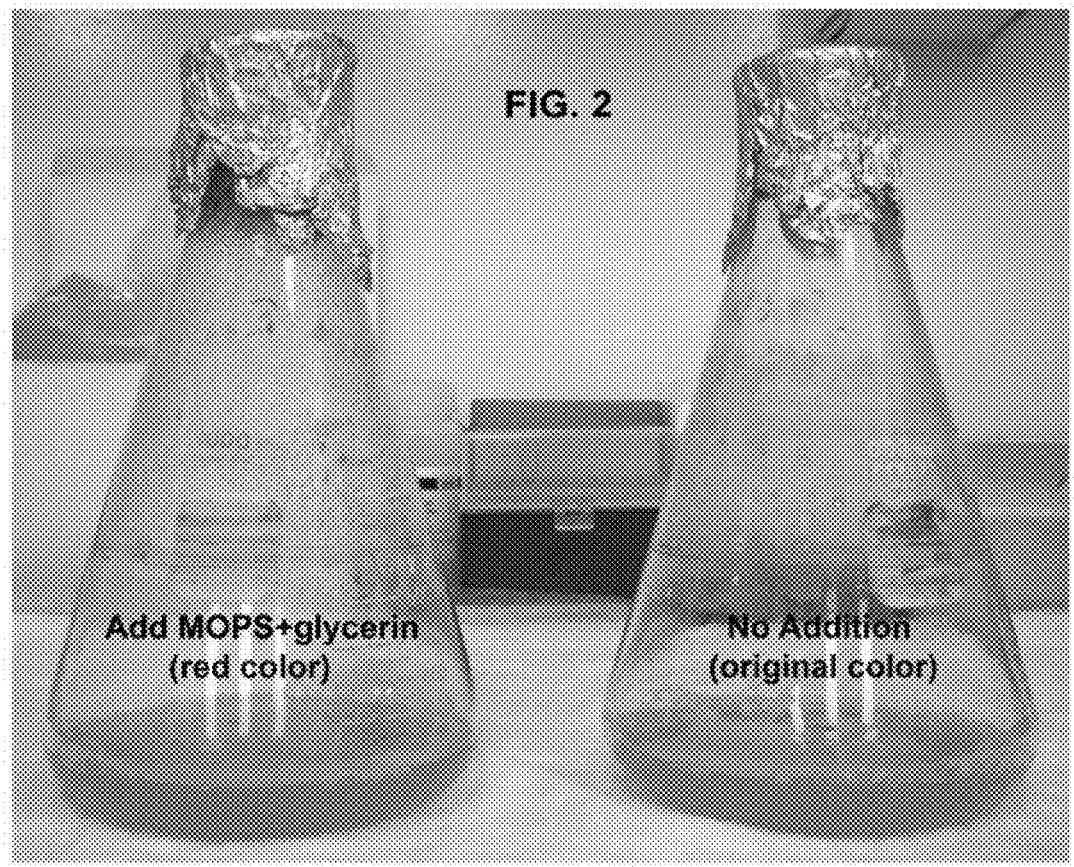
FIG. 2 depicts the results of bacterial culture broths treated with (left) or without (right) the mixture of 0.1% (v/v) MOPS and 0.05% (v/v) glycerin. The E. coli competent cells have been transformed by pLenti-EF1 alpha-RGFP-miR302 before the treatment of chemical inducers.
Figure 3:
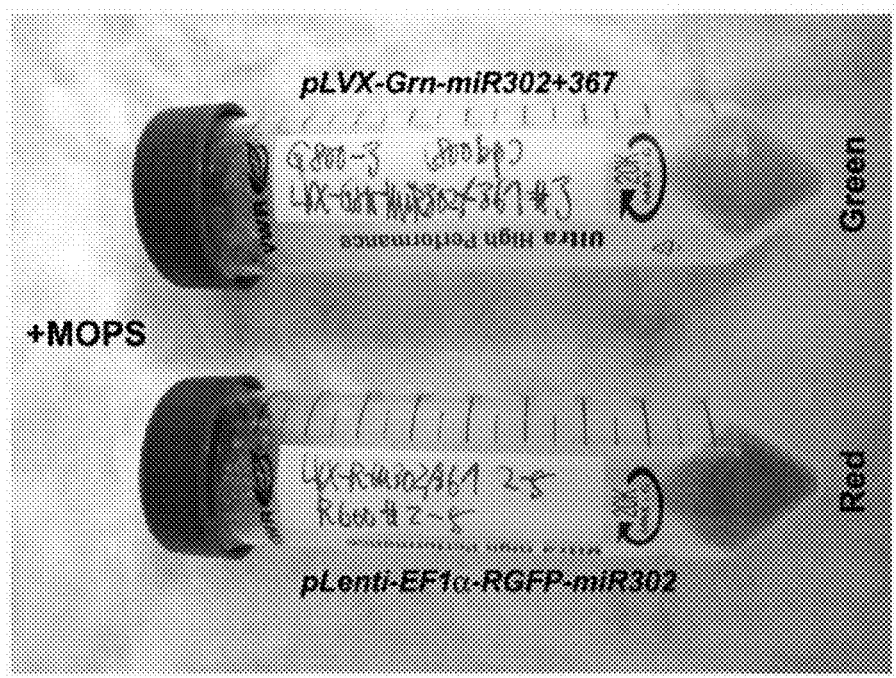
FIG. 3 shows the results of different bacterial pellets after treated with 0.1% (v/v) MOPS. The E. coli competent cells have been transformed by either pLVX-Grn-miR302+367 (green) or pLenti-EF1 alpha-RGFP-miR302 (red) before the MOPS treatment.
Figure 4:
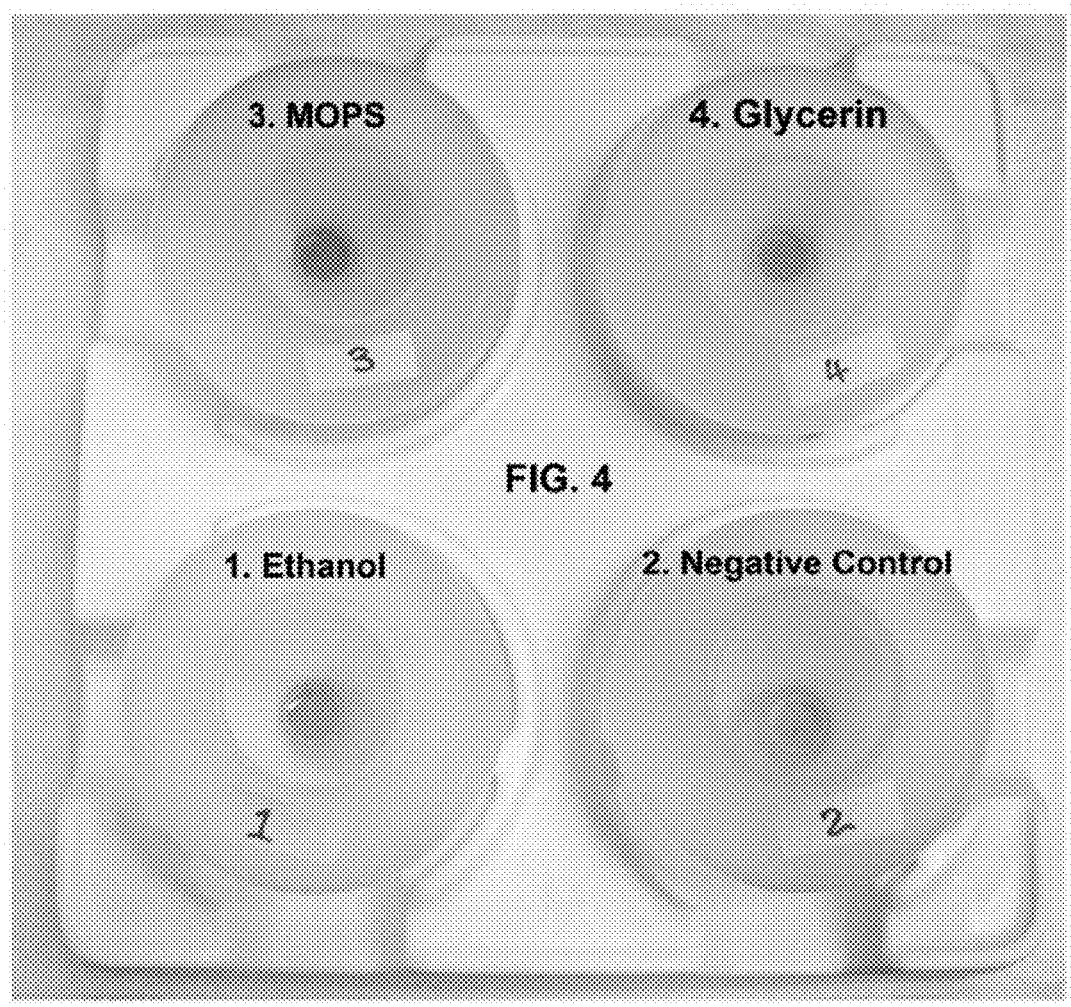
FIG. 4 shows the inducibility of various chemical inducers for inducing pol-2 promoter-driven gene expression in E. coli competent cells. Among all chemicals tested, the top three most potent inducers are MOPS, glycerin and ethanol. The chemical concentration used can be ranged from about 0.001% to 4%, most preferably, from 0.01% to 1%.

*E. coli* DH5alpha competent cells were acquired as a part from the z-competent *E. coli* transformation kit (Zymo Research, Irvine, Calif.) and then transformed by mixing with 5 μg of a pre-made plasmid vector such as pLenti-EF1alpha-RGFP-miR302 or pLVX-Grn-miR302+367. Non-transformed cells were normally grown in Luria-Bertani (LB) broth supplemented with 10 mM $MgSO_4$ and 0.2 mM glucose at 37° C. with frequent agitation at 170 rpm, whereas the transformed cells are cultivated in the above LB broth further supplemented with additional 100 μg/ml ampicillin. For chemical induction, 0.5 to 2 ml of MOPS, glycerin and/or ethanol, respectively or in combination, was added into 1 litter LB broth supplemented with 10 mM $MgSO_4$ and 0.2 mM glucose in the presence of 100 μg/ml ampicillin. For negative control, the transformed cells were cultivated in the above ampicillin-supplemented LB broth but without adding any chemical inducer. The results are shown in FIGS. 2-4.

2. Human Cell Culture and MicroRNA Transfection

Figure 9:
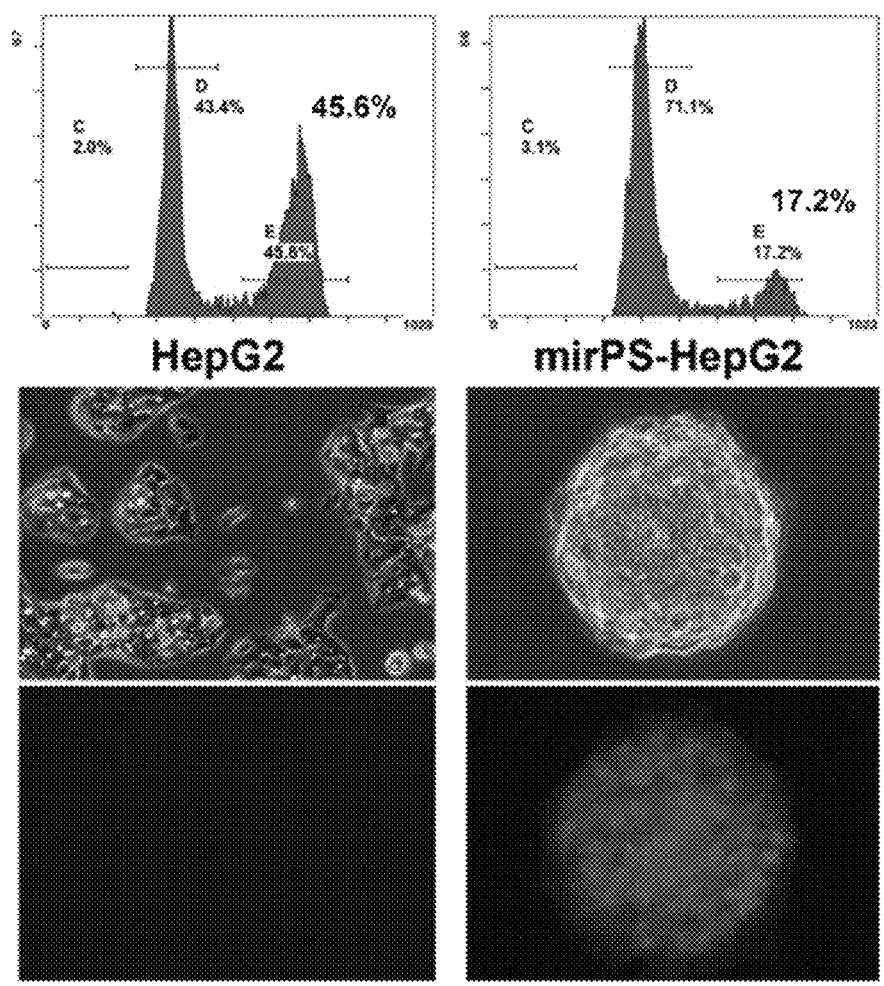
FIG. 9 shows the in vitro tumorigenicity assays of human liver cancer cell line HepG2 in response to miR-302 transfection. The cells obtained after miR-302 transfection are labeled as mirPS-HepG2, indicating the change of their cancer cell properties into an induced pluripotent stem cell (iPSC)-like state. Changes of morphology and cell cycle rate before and after miR-302 transfection were compared. Each cell DNA content respective to cell cycle stages was shown by a peak chart of flow cytometry analysis above the cell morphology (n=3,p<0.01).
Figure 10A:
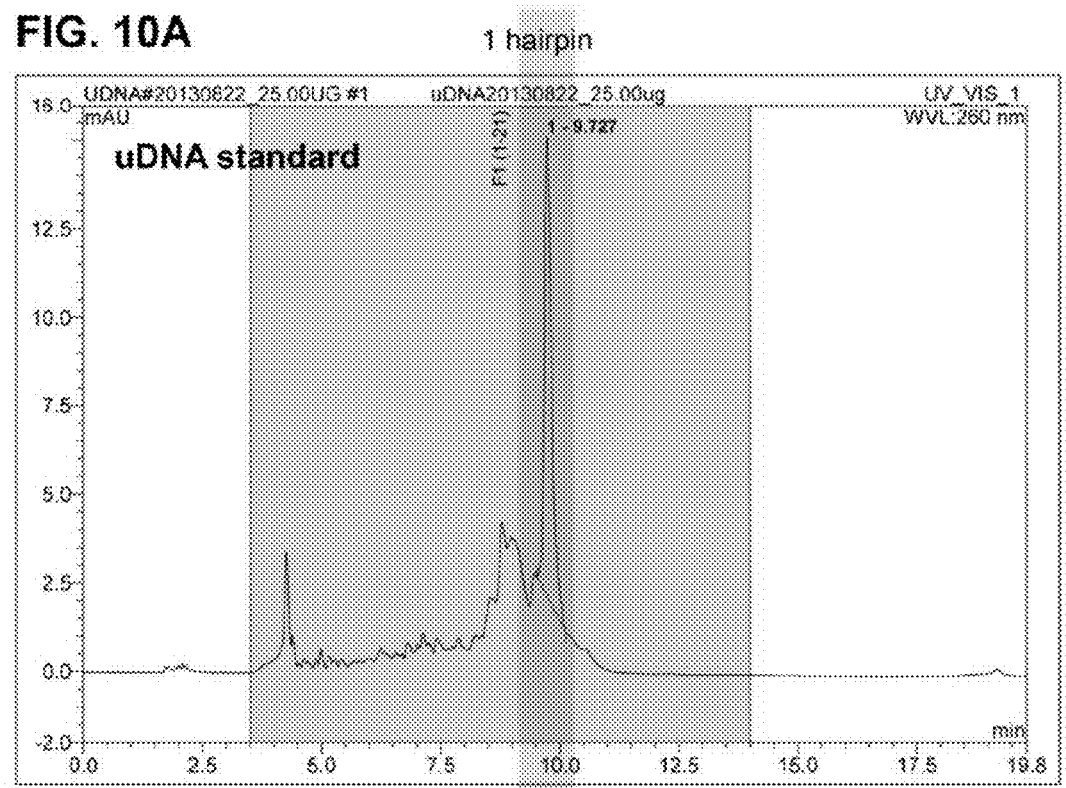
FIGS. 10A and 10B show the results of HPLC purification and analysis using a synthetic standard uDNA (by Sigma-Genosys) and freshly extracted pro-miR-302s isolated from pLenti-EF1alpha-RGFP-miR302-transformed *E. coli* cells. The standard uDNA was designed to be equal to a natural pre-miR-302a as: 5'-CCACCACUUA AACGUGGAUG UACUUGCUUU GAAACUAAAG AAGUAAGUGC UUCCAUGUUU UGGUGAUGG-3' (SEQ.ID.NO.4).
Figure 10B:
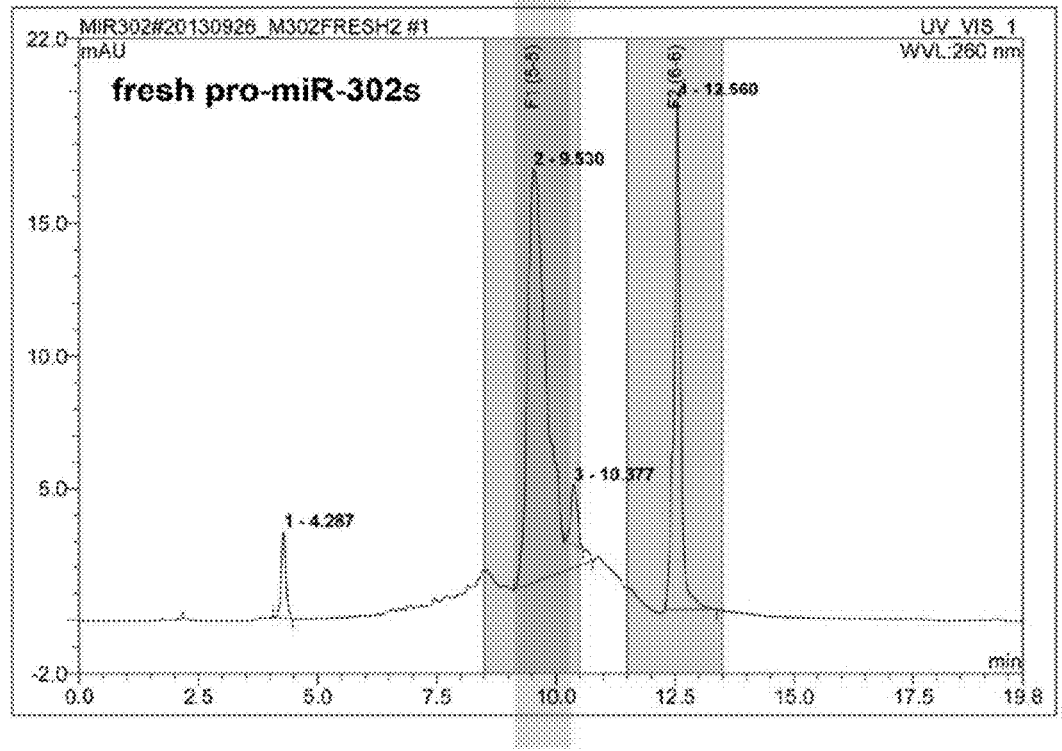

Human liver cancer cell line HepG2 was obtained from ATCC and maintained according to manufacturer's suggestions. For transfection, 15 μg of pre-miR-302 was dissolved in 1 ml of fresh RPMI medium and mixed with 50 μl of X-tremeGENE HP DNA transfection reagent (Roche, Indianapolis, Ind.). After 10 min incubation, the mixture is added into a 100-mm cell culture dish containing 50%~60% confluency of HepG2. The medium was refreshed 12 to 18 hours later. After these transfected cells formed sphere-like iPSC colonies, the medium was changed to a knockout DMEM/F-12 medium (Invitrogen) supplemented with 20% knockout serum, 1% MEM nonessential amino acids, 100 μM β-mercaptoethanol, 1 mM GlutaMax, 1 mM sodium pyruvate, 10 ng/ml bFGF, 10 ng/ml FGF-4, 5 ng/ml LIF, 100 IU/ml penicillin/100 μg/ml streptomycin, 0.1 μM A83-01, and 0.1 μM valproic acid (Stemgent, San Diego, Calif.), and the cells were cultivated at 37° C. under 5% $CO_2$. The result is shown in FIG. 9.

3. Protein Extraction and Western Blot Analysis

Figure 5:
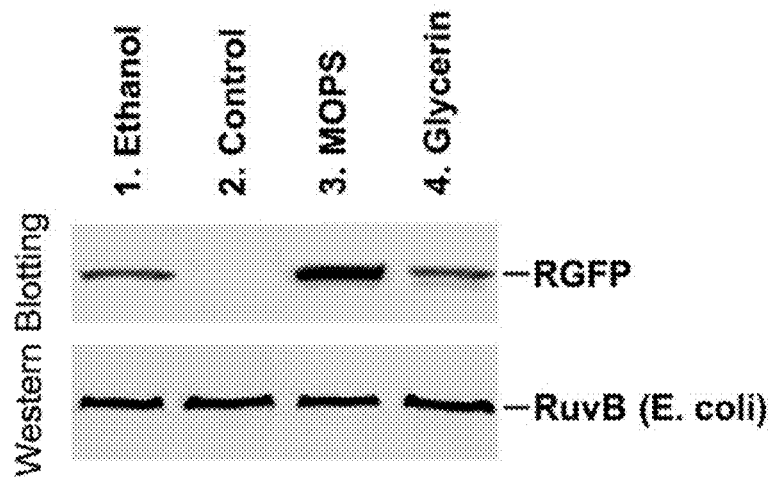
FIG. 5 shows the Western blotting results of red RGFP protein expression induced by MOPS, glycerin and ethanol, respectively. Bacterial RuvB protein was used as a housekeeping standard to normalize the detected RGFP expression. Proteins extracted from blank E. coli cells, i.e. transformed with no vector, were used as a negative control.

Cells ($10^6$) were lysed with a CelLytic-M lysis/extraction reagent (Sigma) supplemented with protease inhibitors, Leupeptin, TLCK, TAME and PMSF, following the manufacturer's suggestion. Lysates were centrifuged at 12,000 rpm for 20 min at 4° C. and the supernatant was recovered. Protein concentrations were measured using an improved SOFTmax protein assay package on an E-max microplate reader (Molecular Devices, CA). Each 30 μg of cell lysate was added to SDS-PAGE sample buffer under reducing (+50 mM DTT) and non-reducing (no DTT) conditions, and boiled for 3 min before loading onto a 6~8% polyacylamide gel. Proteins were resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hours at room temperature. Then, a primary antibody was applied to the reagent and incubated the mixture at 4° C. Primary antibodies included Oct3/4 (Santa Cruz Biotechnology, Santa Cruz, Calif.), RuvB (Santa Cruz) and RGFP (Clontech). After overnight, the membrane was rinsed three times with TBS-T and then exposed to goat anti-mouse IgG conjugated secondary antibody to Alexa Fluor 680 reactive dye (1:2,000; Invitrogen-Molecular Probes), for 1 hour at the room temperature. After three additional TBS-T rinses, fluorescent scanning of the immunoblot and image analysis was conducted using Li-Cor Odyssey Infrared Imager and Odyssey Software v.10 (Li-Cor). The results are shown in FIG. 5.

4. RNA Extraction and Northern Blot Analysis

Figure 6:
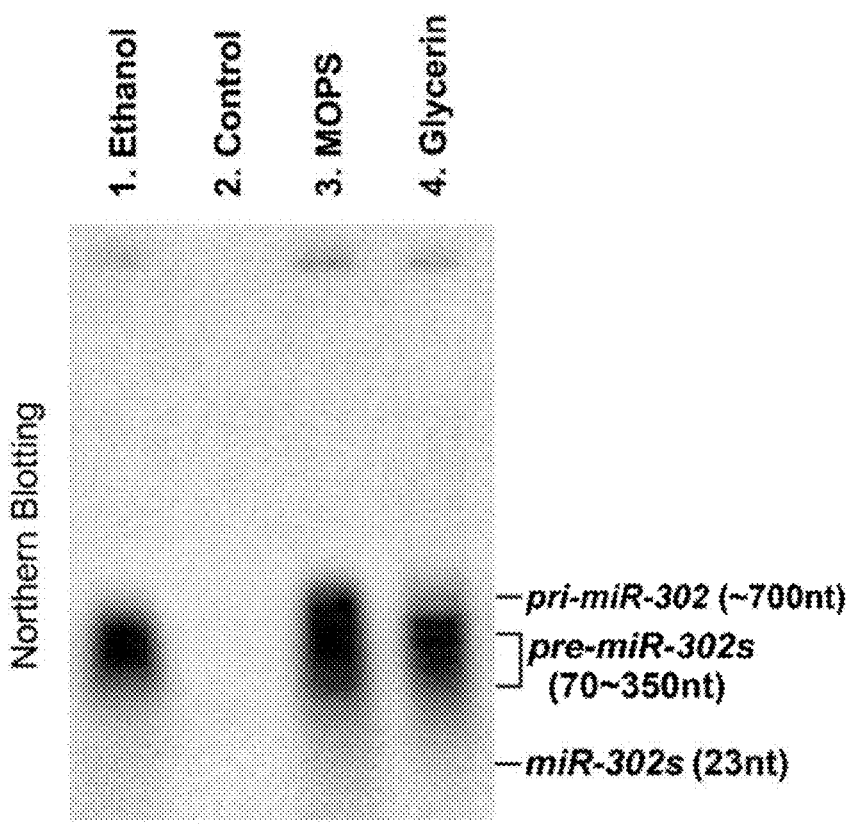
FIG. 6 shows the Northern blotting results of the expression of the miR-302 familial cluster (~700nt) and its derivative precursors (pre-miR-302s with 1 to 4 hairpins) induced by MOPS, glycerin and ethanol, respectively. RNAs extracted from blank E. coli cells were used as a negative control.

Total RNAs (10 μg) were isolated with a mirVana™ miRNA isolation kit (Ambion, Austin, Tex.), fractionated by either 15% TBE-urea polyacrylamide gel or 3.5% low melting point agarose gel electrophoresis, and electroblotted onto a nylon membrane. Detection of miR-302s and the related pre-miR-302s was performed with a [LNA]-DNA probe (5'-[TCACTGAAAC] ATGGAAGCAC TTA-3') (SEQ.ID.NO.10) probe. The probe has been purified by high-performance liquid chromatography (HPLC) and tail-labeled with terminal transferase (20 units) for 20 min in the presence of [$^{32}P$]-dATP (>3000 Ci/mM, Amersham International, Arlington Heights, Ill.). The results are shown in FIG. 6.

5. Plasmid Amplification and Plasmid DNA/Total RNA Extraction

*E. coli* DH5alpha competent cells after transformation (from Example 1) were cultivated in LB broth supplemented with 10 mM $MgSO_4$ and 0.2 mM glucose at 37° C. with frequent agitation at 170 rpm. For inducing eukaryotic promoter-driven RNA transcription, 0.5 to 2 ml of MOPS, glycerin, and/or ethanol was added into every 1 litter of LB broth for propagating the transformed cells overnight. The amplified plasmid DNAs and expressed mRNAs/microR-NAs in the transformed cells were isolated using a HiSpeed plasmid purification kit (Qiagen, Valencia, Calif.), following the manufacturer's protocol but with a minor modification that RNase A was not added into the P1 buffer. After that, the final extracted products containing both plasmids and mRNAs/microRNAs were dissolved in DEPC-treated dd$H_2O$ and stored at −80° C. before use. This forms microRNA-containing cell extracts (CCE). For purifying only the amplified plasmid vectors, RNase A was added into the P1 buffer and the extraction procedure was performed following the manufacturer's protocol.

6. MicroRNA and Pre-miRNA Isolation/Purification

For purifying microRNAs and pre-miRNAs, the total RNAs isolated from Example 5 were further extracted using a mirVana™ miRNA isolation kit (Ambion, Austin, Tex.), following the manufacturer's protocol. The final products so obtained were dissolved in DEPC-treated ddH$_2$O and stored at −80° C. before use. This forms purified microRNA precursors. Because bacterial RNAs are naturally degraded very fast (within a few hours) whereas eukaryotic hairpin-like microRNA precursors (pre-miRNAs and pri-miRNAs) remain largely stable at 4° C. (half-life up to 3-4 days), we can use this half-life difference to acquire relatively pure pri-/pre-miRNAs for other applications. For example, the pre-miR-302s so obtained can be used to reprogram somatic cells to hESC-like iPSCs, as shown in FIG. 9.

7. Immunostaining Assay

Figure 7:
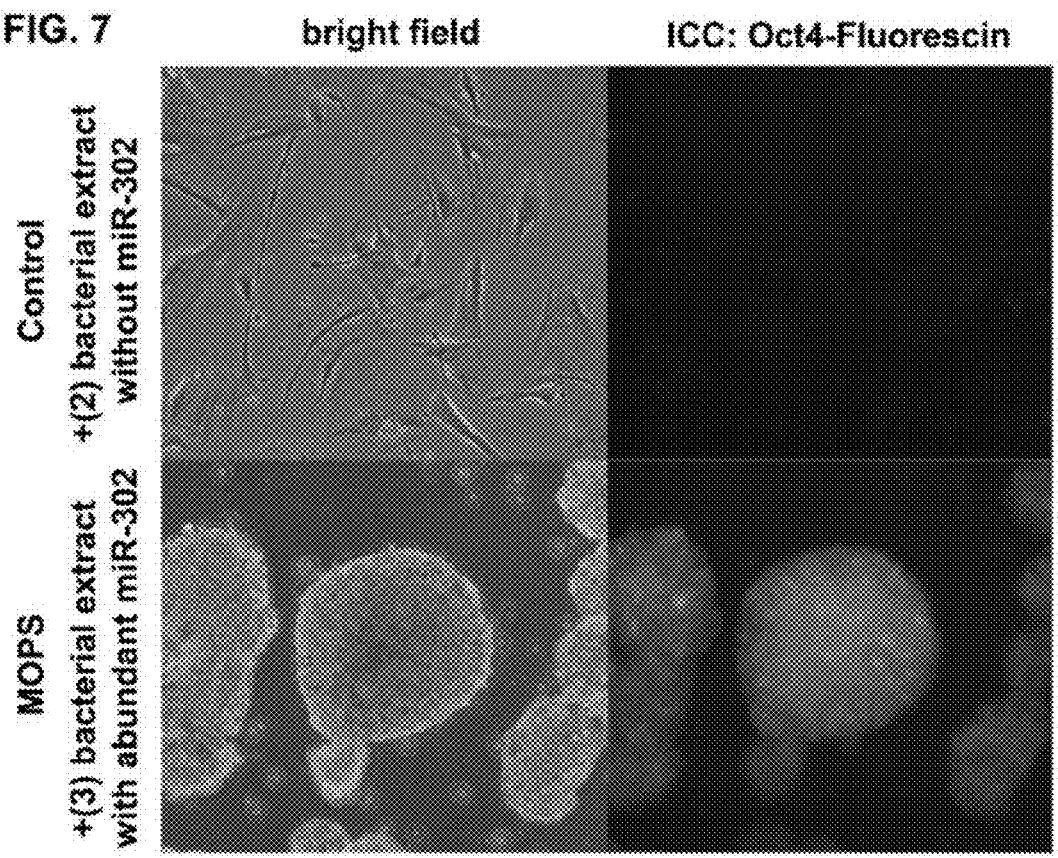
FIG. 7 shows iPSC generation using miR-302 and/or pre-miR-302 isolated from bacterial competent cell extracts (BE), which is confirmed by Northern blot analysis as shown in FIG. 6. As reported, miR-302-reprogrammed iPSCs (or called mirPSCs) form sphere-like cell colonies and express strong Oct4 as a standard hESC marker.

Embedding, sectioning and immunostaining tissue samples were performed as previously reported (Lin et al., 2008). Primary antibodies include Oct4 (Santa Cruz) and RGFP (Clontech, Palo Alto, Calif.). Fluorescent dye-labeled goat anti-rabbit or horse anti-mouse antibody was used as the secondary antibody (Invitrogen-Molecular Probes, Carlsbad, Calif.). Positive results were examined and analyzed at 100× or 200× magnification under a fluorescent 80i microscopic quantitation system with a Metamorph imaging program (Nikon). The result is shown in FIG. 7.

8. Bisulfite DNA Sequencing

Figure 8:
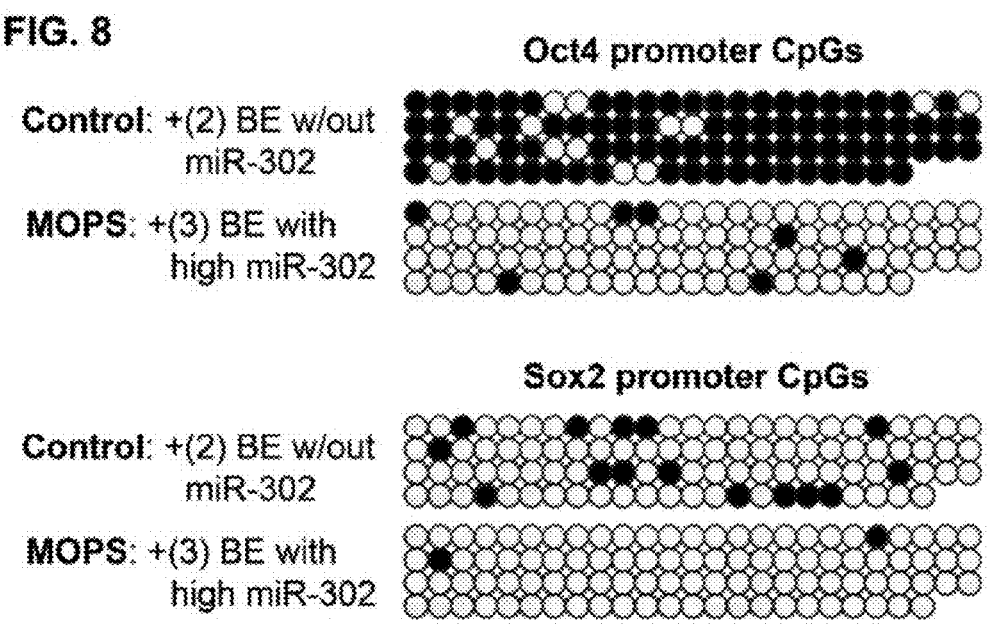
FIG. 8 shows the global DNA demethylation of Oct4 and Sox2 gene promoters induced by the miR-302 and/or pre-miR-302 isolated from bacterial competent cell extracts (BE), which is confirmed by Northern blot analysis as shown in FIG. 6. As demonstrated by Simonsson and Gurdon (*Nat Cell Biol.* 6, 984-990, 2004), both signs of global DNA demethylation and Oct4 expression are required for somatic cell reprogramming to form iPSCs.

Genomic DNAs were isolated from ~2,000,000 cells using a DNA isolation kit (Roche) and 1 µg of the isolated DNAs was further treated with bisulfite (CpGenome DNA modification kit, Chemicon, Temecula, Calif.), following the manufacturers' suggestion. The bisulfite treatment converted all unmethylated cytosine to uracil, while methylated cytosine remained as cytosine. For bisulfite DNA sequencing, we amplified the promoter region of the Oct4 gene with PCR primers: 5'-GAGGCTGGAG CAGAAGGATT GCTTTGG-3' (SEQ.ID.NO.11) and 5'-CCCTCCTGAC CCATCACCTC CACCACC-3' (SEQ.ID.NO.12). For PCR, the bisulfite-modified DNAs (50 ng) were mixed with the primers (total 100 pmol) in 1×PCR buffer, heated to 94° C. for 2 min, and immediately cooled on ice. Next, 25 cycles of PCR were performed as follows: 94° C. for 1 min and 70° C. for 3 min, using an Expand High Fidelity PCR kit (Roche). The PCR product with a correct size was further fractionized by 3% agarose gel electrophoresis, purified by a gel extraction filter (Qiagen), and then used in DNA sequencing. After that, a detailed profile of DNA methylation sites was generated by comparing the unchanged cytosine in the converted DNA sequence to the unconverted one, as shown in FIG. 8.

9. DNA-Density Flow Cytometry

Cells were trypsinized, pelleted and fixed by re-suspension in 1 ml of pre-chilled 70% methanol in PBS for 1 hour at −20° C. The cells were pelleted and washed once with 1 ml of PBS and then pelleted again and resuspended in 1 ml of 1 mg/ml propidium iodide, 0.5 µg/ml RNase in PBS for 30 min at 37° C. After that, about 15,000 cells were analyzed on a BD FACSCalibur (San Jose, Calif.). Cell doublets were excluded by plotting pulse width versus pulse area and gating on the single cells. The collected data were analyzed using the software package Flowjo using the "Watson Pragmatic" algorithm. The result was shown in the top panels of FIG. 9.

10. MicroRNA (miRNA) Microarray Analysis

Figure 11A:
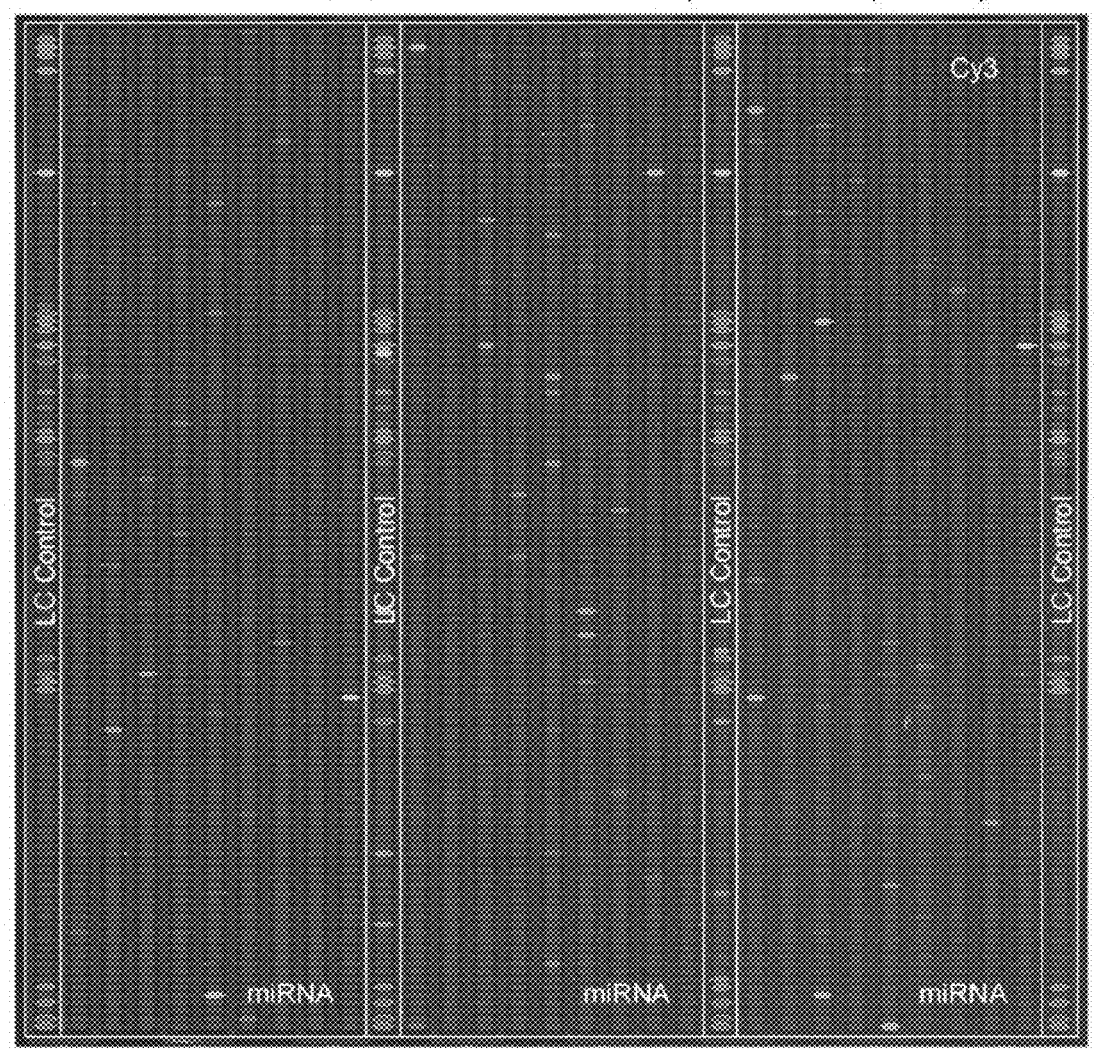
FIGS. 11A and 11B show the results of microRNA (miRNA) microarray analyses using small RNAs extracted from either blank *E. coli* competent cells or pLenti-EF1alpha-RGFP-miR302 (RGFP-miR302)-transfected cells, i.e. the transformed cells. The extracted small RNAs were further purified by HPLC as shown in the green-labeled area of FIG. 10B.
Figure 11B:
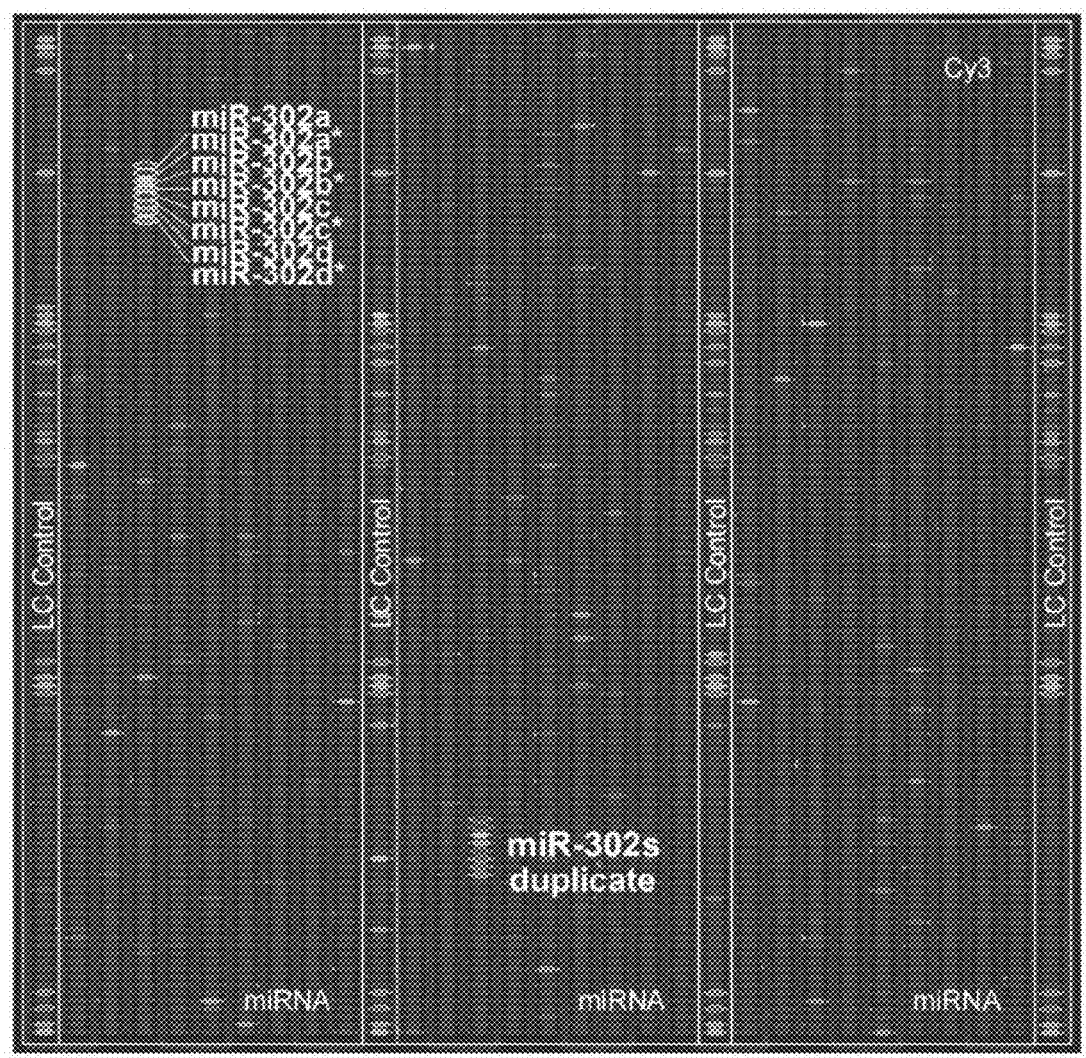
Figure 14:
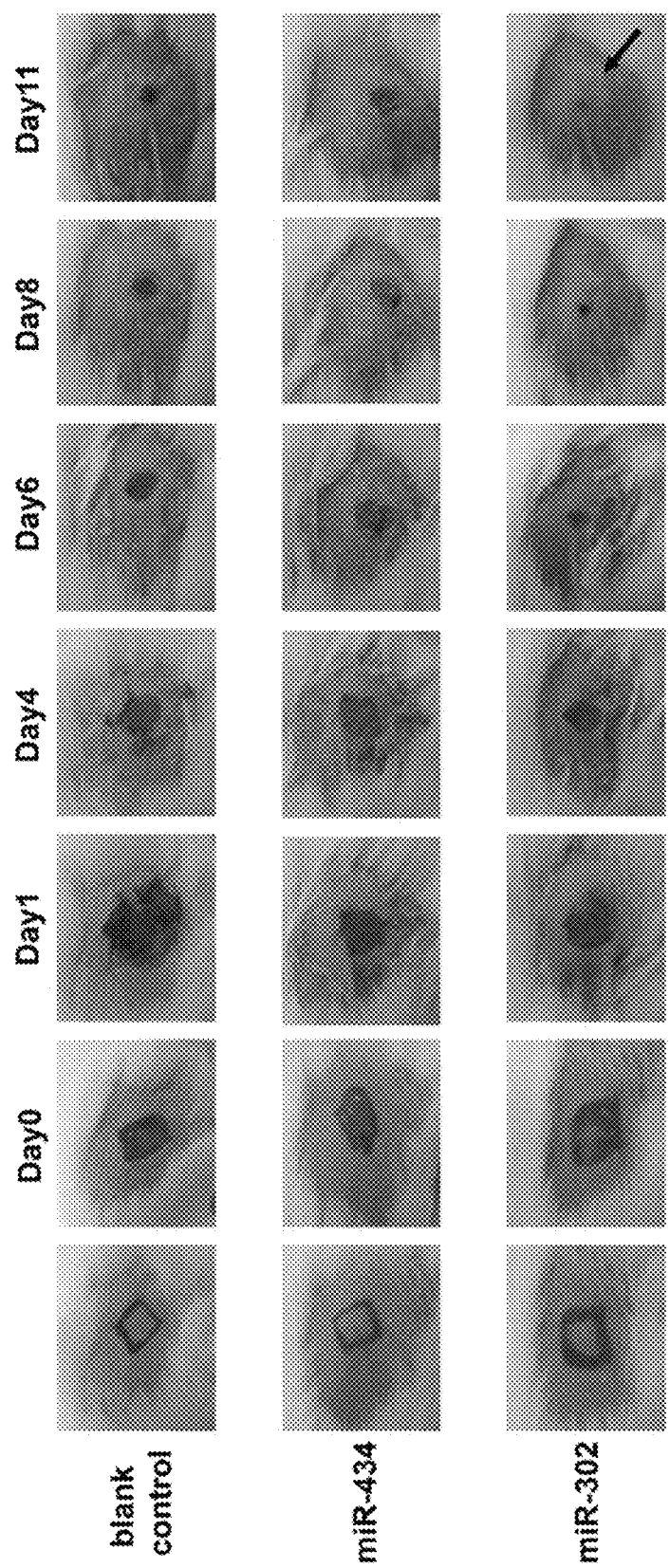
FIG. 14 shows the results of an in-vivo wound healing trial using microRNA miR-302 and/or pre-miR-302 containing ointment to treat skin open wounds in mice. The skin wounds of miR-302 and/or pre-miR-302-treated mice were at least twice larger than those of control mice treated with only blank ointment or other microRNA (miR-HA). The trial results clearly demonstrated that miR-302 and/or pre-miR-302 treatments significantly enhanced the speed of wound healing over two times faster than all other treatments and controls. Moreover, miR-302 and/or pre-miR-302-treated wound healing area showed normal hair regrowth and left no scar while other treatments resulted in minor scars with no hair (indicated by black arrow).
Figure 15:
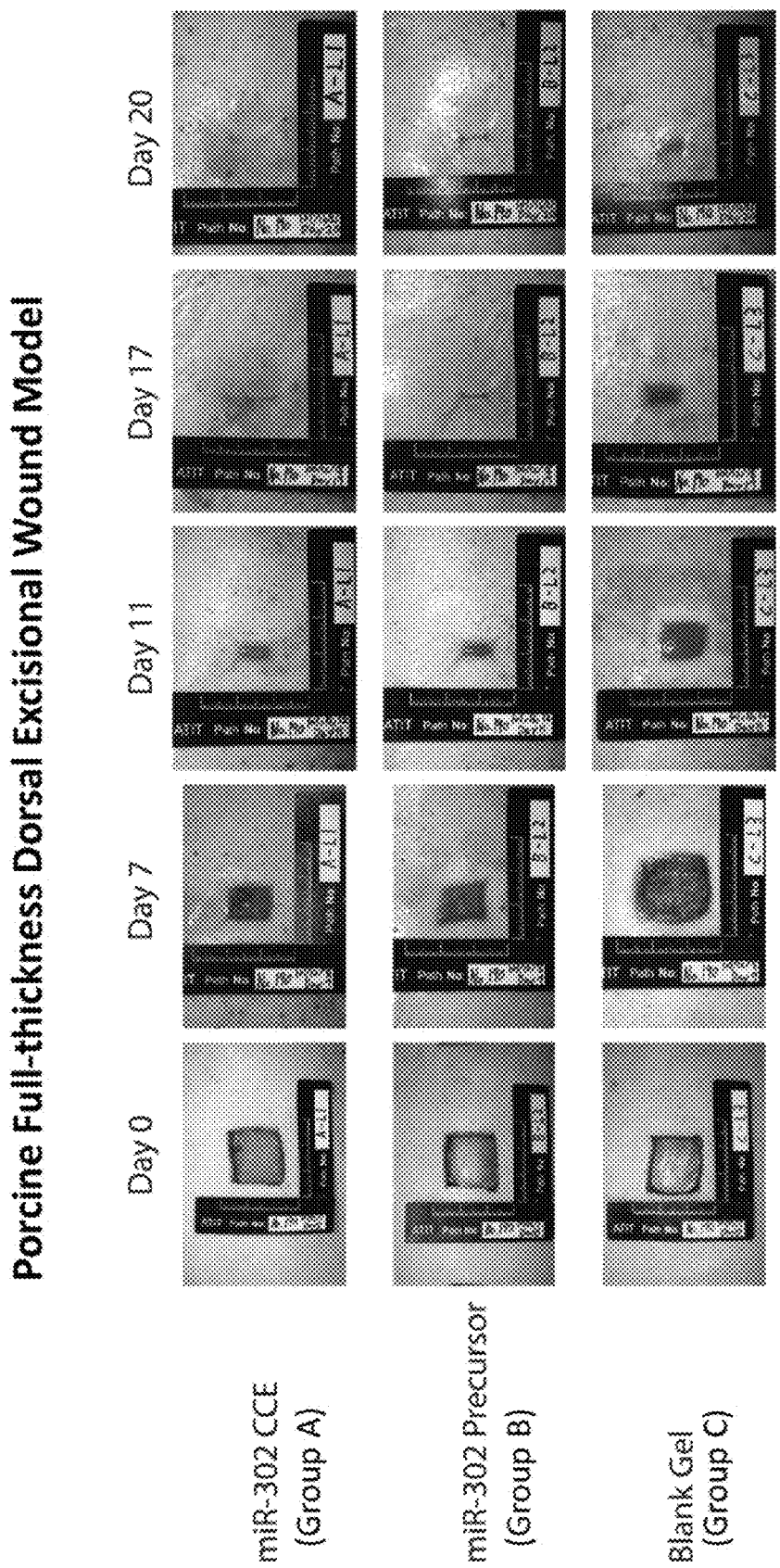
FIG. 15 shows the results of an in-vivo wound healing trial using microRNA miR-302 cell extracts (CCE) or miR-302 precursor-containing F2 ointments/gel to treat skin open wounds in pigs, i.e. efficacy of miR-302 CCE and precursor treatments on closure of full-thickness wounds in pigs, respectively. Six (6) full-thickness square wounds (2 cm×2 cm or 4 cm$^2$ each) were generated on the backside of each animal, with 3 wounds each on the right and left side. The wounds on each side of each animal received topical treatment with F2-formulated miR-302 CCE, F2-formulated miR-302 precursors, or F2 gel alone as blank control, respectively. These treatments were applied on days 0, 1, 2, 3, 4, 5, 7, 9, 11, 14 and 17. This representative graph shows the size of the wounds on the left side in one of the animals used in the study (no. 190) on days 0, 7, 11, 17 and 20.
Figure 16:
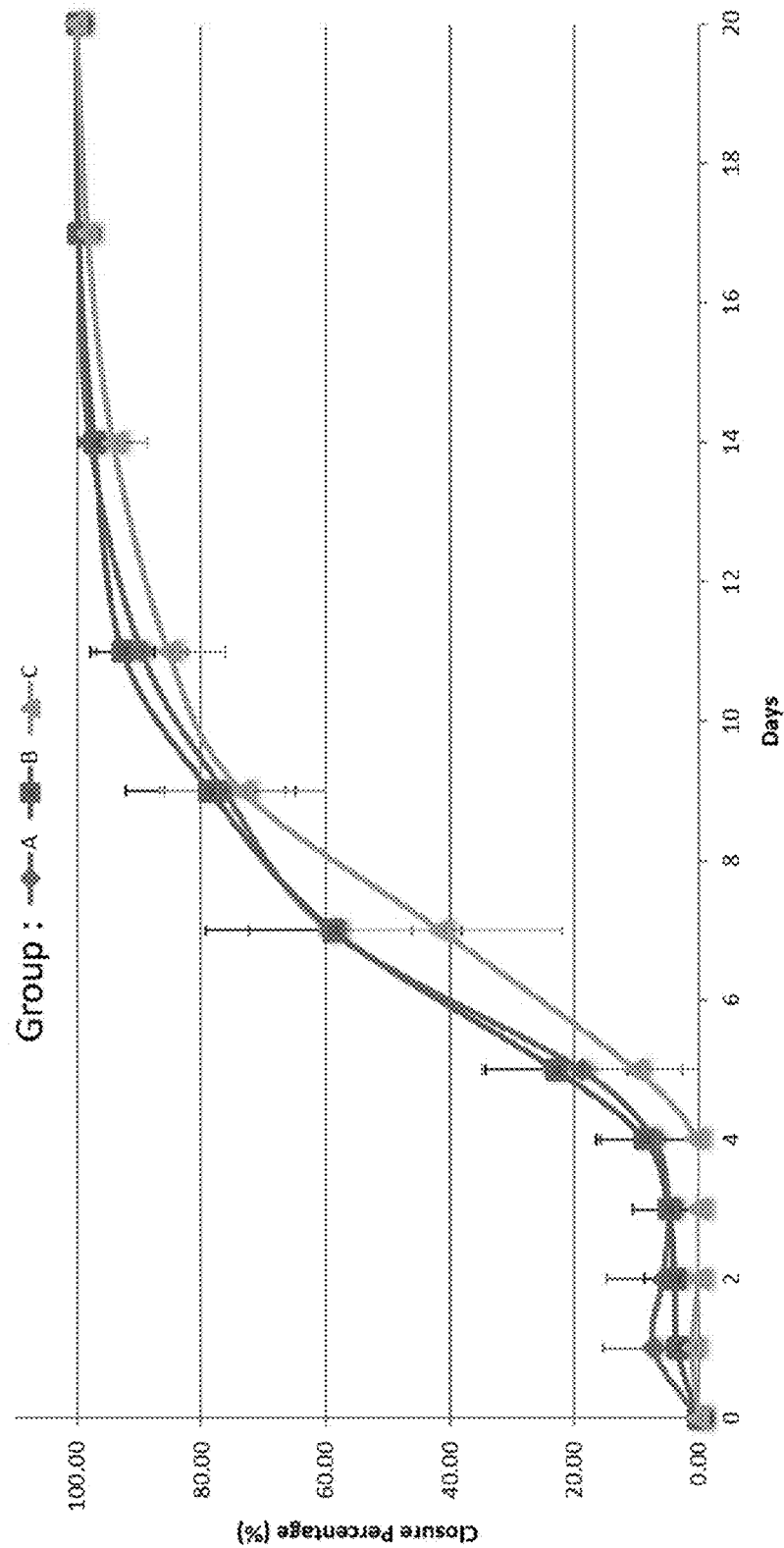
FIG. 16 shows time course of wound closure percentage following treatments with miR-302 CCE (A), miR-302 precursors (B), and F2 gel alone (C), respectively. Establishment of the wounds and subsequent topical treatments with miR-302 CCE, miR-302 precursors and F2 gel alone have been described in detail in Example 12. Photos of each wound were taken on days 0, 1, 2, 3, 4, 5, 7, 9, 11, 14, 17 and 20, respectively, and used for determining the wound area. Percentage of wound healing or closure at each treatment time point was calculated according to the formula (day 0 wound area−day N wound area)/day 0 wound area× 100.

At about 70% confluency, small RNAs from each cell culture were isolated, using the mirVana™ miRNA isolation kit (Ambion). The purity and quantity of the isolated small RNAs were assessed, using 1% formaldehyde-agarose gel electrophoresis and spectrophotometer measurement (Bio-Rad), and then immediately frozen in dry ice and submitted to LC Sciences (San Diego, Calif.) for miRNA microarray analyses. Each microarray chip was hybridized a single sample labeled with either Cy3 or Cy5 or a pair of samples labeled with Cy3 and Cy5, respectively. Background subtraction and normalization were performed as manufacturer's suggestions. For a dual sample assay, a p-value calculation was performed and a list of differentially expressed transcripts more than 3-fold (yellow-red signals) was produced. The final microarray results were shown in FIGS. 11A and 11B, and the list of differentially expressed microRNAs was shown in FIG. 12, which compared the small RNAs extracted from blank E. coli cell lysates (Group 1) to those extracted from pLenti-EF1alpha-RGFP-miR302-transformed cell lysates (Group 2).

11. In Vivo Wound Healing Test in Mouse

The pre-miR-302s and their related plasmid vectors were amplified as described in Examples 1 and 5 and extracted as described in Examples 5 and 6. Then, the isolated pre-miR-302s and their related plasmid vectors were mixed with a pre-prepared ointment base containing cocoa butter, cottonseed oil, olive oil, sodium pyruvate, and white petrolatum. The concentration of miR-302 precursors and vectors in the prepared ointment base is 10 µg/mL. Skin open wounds were generated by scalpel dissection; approximately 0.5-cm for control and 1.0-cm for treated mice. Ointment (about 0.3 mL) was directly applied on the wound and covered the whole wounded area. Then, the treated area was further sealed by liquid bandage.

12. In Vivo Wound Healing Test in Pigs

The Landrace is a white, lop-eared pig breed found in most Central and Eastern European countries. The male Landrace Pigs used for establishing the skin wound models were provided and cared for by ATIT overseen by specially-assigned personnel and qualified veterinarians. Under their supervision, these animals were provided with adequate care in accordance with the Animal Welfare Act in Taiwan. These pigs average 3 months of age and weigh between 18 to 23 kg each. All animals were euthanized at the end of the study.

The animals were anesthetized using Zoletil 50 (6 mg/kg) and their backs were subsequently shaved. Six (6) full-thickness square wounds (2 cm×2 cm or 4 cm$^2$ each) were generated using a sterilized surgical scalpel, with 3 wounds each on the right and left side of each animal. Each wound was received topical treatment with 0.5 mL of either F2-formulated miR-302 CCE (5 mg/mL, group A), F2-formulated miR-302 precursors (1 mg/mL, group B), or F2 gel alone (Blank, group C), respectively. The amount of miR-302 CCE or miR-302 precursors, for example, could be about 200 µl per 4 cm$^2$ wound or more, depending on wound sizes. The treatments were applied on days 0, 1, 2, 3, 4, 5, 7, 9, 11, 14 and 17. Photos of each wound were taken with Sony DSC-H9 camera on days 0, 1, 2, 3, 4, 5, 7, 9, 11, 14, 17 and 20. The area of each wound at each time point was determined using the Image Pro Plus 7.0 imaging software. Percentage of wound healing or closure at each treatment time point was calculated according to the formula: (day 0 wound area−day N wound area)/day 0 wound area×100. Also, tissue samples were collected from each wound and soaked in 10% (v/v) formalin solution before being used for preparing histological sections for H&E staining.

Mean of each test group was calculated by AVERAGE from Microsoft Excel. Standard deviation was calculated using STDEV. Comparisons between the treatment groups were performed using the one-way ANOVA technique, with either a post hoc Dunnet's t-test analysis for comparison to control or a post hoc Tukey analysis for comparison among the 3 treatment groups.

13. Statistic Analysis

Any change over 75% of signal intensity in the analyses of immunostaining, western blotting and northern blotting was considered as a positive result, which in turn is analyzed and presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ was considered significant. All p values were determined from two-tailed tests.

REFERENCES

1. Lin S L and Ying S Y. (2006) Gene silencing in vitro and in vivo using intronic microRNAs. Ying S Y. (Ed.) *MicroRNA protocols*. Humana press, Totowa, N.J., pp 295-312.
2. Lin S L, Chang D and Ying S Y. (2006) Transgene-like animal models using intronic microRNAs. Ying S Y. (Ed.) *MicroRNA protocols*. Humana press, Totowa, N.J., pp 321-334.
3. Lin S L, Chang D, Chang-Lin S, Lin C H, Wu D T S, Chen D T, and Ying S Y. (2008) Mir-302 reprograms human skin cancer cells into a pluripotent ES-cell-like state. *RNA* 14, 2115-2124.
4. Lin S L and Ying S Y. (2008) Role of mir-302 microRNA family in stem cell pluripotency and renewal. Ying S Y. (Ed.) *Current Perspectives in MicroRNAs*. Springer Publishers press, New York, pp 167-185.
5. Lin S L, Chang D, Ying S Y, Leu D and Wu D T S. (2010) MicroRNA miR-302 inhibits the tumorigenicity of human pluripotent stem cells by coordinate suppression of CDK2 and CDK4/6 cell cycle pathways. *Cancer Res.* 70, 9473-9482.
6. Lin S L, Chang D, Lin C H, Ying S Y, Leu D and Wu D T S. (2011) Regulation of somatic cell reprogramming through inducible mir-302 expression. *Nucleic Acids Res.* 39, 1054-1065.
7. McDowell et al. (1994) Determination of intrinsic transcription termination efficiency by RNA polymerase elongation rate. *Science* 266, 822-825.
8. Simonsson S and Gurdon J. (2004) DNA demethylation is necessary for the epigenetic reprogramming of somatic cell nuclei. *Nat Cell Biol.* 6, 984-990.
9. Takahashi et al. (2006). Induction of pluripotent stem cells from mouse embryonic and adult fibroblast cultures by defined factors. *Cell* 126, 663-676.
10. Wang et al. (2008). Embryonic stem cell-specific microRNAs regulate the G1-S transition and promote rapid proliferation. *Nat. Genet.* 40, 1478-1483.
11. Wernig et al. (2007). In vitro reprogramming of fibroblasts into a pluripotent ES-cell-like state. *Nature* 448, 318-324.
12. Yu et al. (2007). Induced pluripotent stem cell lines derived from human somatic cells. *Science* 318, 1917-1920.
13. U.S. Pat. No. 7,959,926 to Buechler.
14. U.S. Pat. No. 7,968,311 to Mehta.
15. European Patent No. EP 2198025 to Lin.
16. U.S. patent application Ser. No. 12/149,725 to Lin.
17. U.S. patent application Ser. No. 12/318,806 to Lin.
18. U.S. patent application Ser. No. 12/792,413 to Lin.
19. U.S. patent application Ser. No. 13/572,263 to Lin.
20. U.S. patent application Ser. No. 13/964,705 to Lin.
21. U.S. Patent Application Publication No. 2007/0099277 to Anderson et al.
22. U.S. Pat. No. 4,879,226 to Wallace et al.

The invention claimed is:

1. A method for enhancing wound healing in vivo using hairpin-like microRNA precursor (pre-miRNA), comprising:
   (a) producing the hairpin-like microRNA precursor in *Escherichia coli* (*E. coli*) strain competent cells having at least an expression vector encoding the hairpin-like microRNA precursor comprising SEQ ID NO:3 operably linked to a CMV promoter or a eukaryotic EF1alpha promoter that is induced by a chemical agent containing 3-morpholinopropane-1-sulfonic acid (MOPS);
   (b) providing at least a hairpin-like microRNA precursor comprising SEQ ID NO:3 that is produced in (a);
   (c) providing at least a wounded or damaged tissue cell in vivo; and
   (d) contacting the hairpin-like microRNA precursor of (b) with the at least a wounded or damaged tissue cell of (c), so as to induce a wound healing effect of the hairpin-like microRNA precursor on the at least one wounded or damaged tissue cell.

2. The method as defined in claim 1, wherein said expression vector is pLenti-EF1alpha-RGFP-miR302.

3. The method as defined in claim 1, wherein said hairpin-like microRNA precursor comprises a hairpin-like sequence of SEQ ID NO:8.

4. The method as defined in claim 1, wherein said hairpin-like microRNA precursor is a miR-302 precursor (pre-miR-302).

5. The method as defined in claim 4, wherein said pre-miR-302 comprises a sequence of miR-302a.

6. The method as defined in claim 4, wherein said pre-miR-302 is capable of being used as a part of drug ingredients for pharmaceutical and therapeutic applications.

7. The method as defined in claim 1, wherein said hairpin-like microRNA precursor is capable of being used as a part of drug ingredients for pharmaceutical and therapeutic applications.

8. The method as defined in claim 1, wherein the hairpin-like microRNA precursor is capable of treating wounds in mammals.

* * * * *